(12) United States Patent
Barnes et al.

(10) Patent No.: US 11,257,209 B2
(45) Date of Patent: Feb. 22, 2022

(54) CANCER RISK STRATIFICATION BASED ON HISTOPATHOLOGICAL TISSUE SLIDE ANALYSIS

(71) Applicant: Ventana Medical Systems, Inc., Tucson, AZ (US)

(72) Inventors: Michael Barnes, Oro Valley, AZ (US); Srinivas Chukka, San Jose, CA (US); Bonnie LaFleur, Tucson, AZ (US); Chang Xu, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 1080 days.

(21) Appl. No.: 15/613,113

(22) Filed: Jun. 2, 2017

(65) Prior Publication Data

US 2017/0270666 A1   Sep. 21, 2017

Related U.S. Application Data

(63) Continuation of application No. PCT/EP2015/078541, filed on Dec. 3, 2015.

(60) Provisional application No. 62/087,229, filed on Dec. 3, 2014.

(51) Int. Cl.
| | |
|---|---|
| *G06T 7/00* | (2017.01) |
| *G16H 50/30* | (2018.01) |
| *G06K 9/62* | (2006.01) |
| *G06K 9/00* | (2006.01) |
| *G06T 7/12* | (2017.01) |
| *G01N 33/574* | (2006.01) |
| *G06T 7/11* | (2017.01) |

(52) U.S. Cl.
CPC ..... *G06T 7/0012* (2013.01); *G01N 33/57415* (2013.01); *G06K 9/00147* (2013.01); *G06K 9/6265* (2013.01); *G06T 7/12* (2017.01); *G16H 50/30* (2018.01); *G01N 2800/52* (2013.01); *G01N 2800/54* (2013.01); *G06T 7/11* (2017.01); *G06T 2207/10056* (2013.01); *G06T 2207/30024* (2013.01)

(58) Field of Classification Search
None
See application file for complete search history.

(56) References Cited

U.S. PATENT DOCUMENTS

| | | |
|---|---|---|
| 2012/0076390 A1 | 3/2012 | Potts et al. |
| 2013/0310267 A1 | 11/2013 | Gustavson |

FOREIGN PATENT DOCUMENTS

| | | |
|---|---|---|
| WO | WO2008/108059 A1 | 6/2010 |
| WO | WO2014102130 A1 | 7/2014 |
| WO | 2014140085 A1 | 9/2014 |

OTHER PUBLICATIONS

Klauβ, Miriam, et al. "Value of three-dimensional reconstructions in pancreatic carcinoma using multidetector CT: initial results." World journal of gastroenterology: WJG 15.46 (2009): 5827.*
Van Meir, Erwin, et al. "Human glioblastoma cells release interleukin 6 in vivo and in vitro." Cancer research 50.20 (1990): 6683-6688.*
Yeung, Y. T., et al. "Interleukins in glioblastoma pathophysiology: implications for therapy." British journal of pharmacology 168.3 (2013): 591-606.*
Chalkidou, A1, et al. "Correlation between Ki-67 immunohistochemistry and 18F-fluorothymidine uptake in patients with cancer: a systematic review and meta-analysis." European journal of cancer 48.18 (2012): 3499-3513.*
International Preliminary Report on Patentability dated Jun. 6, 2017 in corresponding PCT/EP2015/078541 (32467 WO), pp. 1-9.
International Search Report and Written Opinion dated Mar. 3, 2016 in corresponding PCT/E P2015/078541 (32467 WO), pp. 1-16.
Mizuno, Yoshio, Et Al., Standadized Assessment of Ki-67 in Breast Cancer Patients Using Virtual Slides and an Automated Analyzer in Comparison to Central/Local Pathological Assessments, Journal of Cancer Therapy, (2014), 141-146, 05.
Molin, Jesper, et al., Feature-enhancing zoom to facilitate Ki-67 hot spot detection, Progress in Biomedical Optics and Imaging SPIE, (2014), 90410W-90410W, 9041.
Romero, Quinci, Et Al., A novel model for Ki67 assessment in breast cancer, Diagnostic Pathology, (2014), 118, 9.
Sarkar, Anindya, et al., A Robust Method for Inter-Marker Whole Slide Registration of Digital Pathology Images Using Lines Based Features, 2014 IEEE 11th Internat. Symposium on Biomedical Imaging (ISBI), (2014), 762-765, -.
Royston, et al., *External validation of a Cox prognostic model: principles and methods*, BMC Medical Research Methodology, Mar. 6, 2013, doi: 10.1186/1471-2288-13-33, 15 pages.
Tsujitani; Masaaki, *Analysis of Survival Data Having Time-Dependent Covariates*. IEEE Transactions On Neural Networks, vol. 20, No. 3, Mar. 2009, 6 pages.

* cited by examiner

*Primary Examiner* — G Steven Vanni
(74) *Attorney, Agent, or Firm* — Kilpatrick Townsend & Stockton LLP

(57) ABSTRACT

The subject disclosure presents systems and computer-implemented methods for providing reliable risk stratification for early-stage cancer patients by predicting a recurrence risk of the patient and to categorize the patient into a high or low risk group. A series of slides depicting serial sections of cancerous tissue are automatically analyzed by a digital pathology system, a score for the sections is calculated, and a Cox proportional hazards regression model is used to stratify the patient into a low or high risk group. The Cox proportional hazards regression model may be used to determine a whole-slide scoring algorithm based on training data comprising survival data for a plurality of patients and their respective tissue sections. The coefficients may differ based on different types of image analysis operations applied to either whole-tumor regions or specified regions within a slide.

15 Claims, 8 Drawing Sheets

CANCER RISK STRATIFICATION BASED ON HISTOPATHOLOGICAL TISSUE SLIDE ANALYSIS

CROSS-REFERENCE TO RELATED APPLICATIONS

This patent application is a continuation of International Patent Application No. PCT/EP2015/078541 filed Dec. 3, 2015, which claims priority to the benefit of U.S. Provisional Patent Application No. 62/087,229, filed Dec. 3, 2014. Each of the above patent applications is incorporated herein by reference as if set forth in its entirety.

BACKGROUND OF THE SUBJECT DISCLOSURE

Field of the Subject Disclosure

The present subject disclosure relates to computational pathology. More particularly, the present subject disclosure relates to predicting the risk of cancer recurrence among early-stage patients using histopathological images of tissue sections and patient survival outcome data.

Background of the Subject Disclosure

Biological specimens such as tissue sections, blood, cell cultures and the like may be stained with one or more stains to identify and quantify biomarker expressions in the tissue and subsequently analyzed by viewing or imaging the stained specimens. Observing the stained specimens, in combination with additional clinical information, enables diagnosis of disease, prognostic and/or predictive assessment of response to treatment, and assists in the development of new drugs to fight disease. As used herein, a target or target object is a feature of the specimen that a stain identifies. A target or target object may be a protein, protein fragment, nucleic acid, or other object of interest recognized by an antibody, a molecular probe, or a non-specific stain. Those targets that are specifically recognized may be referred to as biomarkers in this subject disclosure. Some stains do not specifically target a biomarker (e.g., the counterstain Hematoxylin which stains all the nuclei in tissue). While hematoxylin has a fixed relationship to its target, most immunohistochemical biomarkers can be identified with a choice of stain. A particular biomarker could be visualized using a variety of stains depending on the particular needs of the assay.

Patients with localized (early stage, resectable) breast cancer undergoing curative surgery and/or therapy have an underlying risk of local or distant cancer recurrence while those patients who experience recurrence exhibit an increased mortality rate. Depending on the size of risk, different treatment options exist. Thus, an assay that allows one to reliably identify patients with a low or high risk of cancer recurrence is needed. Accordingly, technologies are also needed that can reliably discriminate between high and low risk patients and provide healthcare providers with additional information to consider when determining a patient's treatment options.

SUMMARY OF THE SUBJECT DISCLOSURE

The present invention provides for an computational pathology system, where a digital pathology system is used to digitizing cancer biopsy tissue samples followed with using image analysis workflow methods for analyzing the digitized tissue slides and statistical analysis methods to correlate the obtained biomarker expressions in the tissue samples with the patient survival outcome information to construct and clinical use a prognostic model for a prognostic and predictive evaluation of cancer tissue samples, such as early stage cancer prognosis, as claimed in the independent claims. Embodiments of the invention are given in the dependent claims.

The subject disclosure presents systems and computer-implemented methods for providing reliable risk stratification for early-stage breast cancer patients by constructing a prognostic model to predict a recurrence risk of the patient and to categorize the patient into a high or low risk group. A risk stratification system may be trained using training cohort that includes histopathological (H&E and IHC) tissue slides from several patients along with survival outcome data for said patients. The tissue slides may be processed according to a specific staining protocol, digitized on a bright field or fluorescent microscopic or whole slide scanner, and analyzed using automated image analysis algorithms to quantify stains or biomarker expressions in the tissue slides. Quantifying expression may be accomplished using a specific scoring protocol wherein the multiple slide scores may be combined to determine a risk stratification score. The risk stratification system may include a proportional hazards regression module that is used to generate an overall scoring algorithm for the patient which combines the information from all the tissue slide scores and statistically correlating against the survival outcome data for the patients in the training cohort. The proportional hazards regression module may include a Cox proportional hazards model A cutoff point may be computed on the risk stratification score which may comprise optimally stratifying the training patient sample set into low and high risk groups by maximizing the separation between the Kaplan-Meier survival probability estimate curves between them. Subsequently, any single patient's tissue slides that are processed using the same staining protocol, digitized, followed with image analysis and/or scores generated according to the scoring protocol may be combined and analyzed using the risk stratification scoring algorithm generated during the training process, and stratified using the generated cutoff point to predict a survival probability and/or prognosis for the single patient.

In one exemplary embodiment, the subject disclosure includes an image analysis system and computer implemented method for early stage cancer prognosis. Digitized whole slide images of serial section tissue slides are stained with the desired set of histopathological assays (H&E, IHC) utilizing either simplex or multiplex methodologies to evaluate the tumor and immune marker expressions in the tissue. Such staining methods may include, for example, (1) mapping one or more regions (all the tumor regions on the whole slide, specific "marker hotspots" i.e., tumor sub-regions where a particular marker is over-expressed, immune specific regions from the tissue microenvironment, stromal regions which are adjacent to tumor regions) annotated on a digitized image of the first tissue slide (example, H&E slide or Ki67 slide) or subset of a selected few slides (like H&E and Ki-67) to digitized images of each of a plurality of tissue slides, wherein the plurality of tissue slides correspond to serial sections from a tissue block; (2) and computing a whole slide score for the plurality of tissue slides by scoring using marker-specific image analysis algorithms to quantify the expression of one or more tumor markers or immune markers on each tissue slide; where the computed marker expression is quantified in terms of commonly used whole slide score metric (marker percentage positivity, H-score, absolute or relative count or density of particular cell type etc.); and (3) computing the risk stratification score by combining the whole slide scores using a mathematical formula and with a set of combining coefficients as determined by the prognostic model wherein a patient may be stratified into a low or high recurrence risk group based on a cut-off point of the risk stratification score.

In another exemplary embodiment, the subject disclosure comprises a system for early stage cancer prognosis. The system includes a processor; and a memory coupled to the processor, the memory configured to store computer-readable instructions that, when executed by the processor, cause the processor to perform operations comprising: generating a set of whole tumor regions on a H&E tissue slide, where the whole tumor regions can be either manually annotated by a pathologist on a digitized whole slide in a whole slide image reviewing system using the annotation tools or generated using an image analysis algorithm to automatically detect and identify the whole tumor regions; registering a whole-tumor region annotated on an H&E slide with each of a plurality of adjacent tissue slides and mapping the annotations to each of them; and using image analysis algorithms to analyze and generating a whole slide score for marker expression on each of the plurality of adjacent IHC tissue slides such as percentage positivity, H-score, total cell counts; generating a risk stratification score by combining the whole slide scores from the IHC slides using a mathematical formula with a set of coefficients, where the coefficient values are determined based on a statistical fit of the risk stratification score against the survival data for a plurality of patients using a Cox proportional hazard regression model to construct a prognostic model; and applying the derived prognostic model to a test series of images associated with a single patient, the test series of images also being annotated with the whole tumor workflow.

In yet another exemplary embodiment, the subject disclosure is comprises a tangible non-transitory computer-readable medium to store computer-readable code that is executed by a processor to perform operations. The system includes a processor and a memory coupled to the processor, the memory configured to store computer-readable instructions that, when executed by the processor, cause the processor to perform operations comprising: generating a set of "hot spots" regions on Ki67 tissue slide, where the hot spots reflect the invasive and aggressive tumor regions with high Ki67 marker expression and the spatial variability of marker expression in the tumor regions in the slide; the "hot spots" can be manually annotated by a pathologist on a digitized whole slide in a whole slide image reviewing system using the annotation tools or automatically generated by an image analysis algorithm to detect Ki67 stained tumor cells and over expressive regions; registering these hot spots annotated on Ki67 tissue slide with each of a plurality of adjacent tissue slides to map the annotated regions; generating a risk stratification score by combining the whole slide scores from the plurality of whole slide scores using a mathematical formula with a set of coefficients, where the coefficient values are specific to the type of annotations and workflow and are determined based on operations involving a statistical fit of the risk stratification score against the survival data using on Cox proportional hazards model for a plurality of training patients to construct a prognostic model; and applying the prognostic model to a test series of images associated with a single patient, the test series of images also being annotated with the Ki-67 hotspot workflow.

A 'tissue sample' as understood herein is any biological sample obtained from a tissue region, such as a surgical biopsy specimen that is obtained from a human or animal body for anatomic pathology. The tissue sample may be a prostrate tissue sample, a breast tissue sample, a colon tissue sample or a tissue sample obtained from another organ or body region.

A 'multi-channel image' as understood herein encompasses a digital image obtained from a biological tissue sample in which different biological structures, such as nuclei and tissue structures, are simultaneously stained with specific fluorescent dyes, each of which fluoresces in a different spectral band thus constituting one of the channels of the multi-channel image. The biological tissue sample may be stained by a plurality of stains and/or by a stain and a counterstain, the later being also referred to as a "single marker image".

An 'unmixed image' as understood herein encompasses a grey-value or scalar image obtained for one channel of a multi-channel image. By unmixing a multi-channel image one unmixed image per channel is obtained.

A 'color channel' as understood herein is a channel of an image sensor. For example, the image sensor may have three color channels, such as red (R), green (G) and blue (B).

A 'hot spot' as understood herein is a region in a stained image that has a high intensity value and/or high variation of intensity values which signals a high tumor growth rate.

For example, Ki-67 hot spot detection is as such known from the prior art, cf. Khan Niazi M K, Yearsley M M, Zhou X, Frankel W L, Gurcan M N. Perceptual clustering for automatic hotspot detection from Ki-67-stained neuroendocrine tumour images. J Microsc. 2014 December; 256(3): 213-25. doi: 10.1111/jmi.12176. Epub 2014 Sep 16. PMID: 25228134.

A 'field of view (FOV)' as understood herein encompasses an image portion that has a predetermined size and shape, such as a rectangular or circular shape. In accordance with embodiments of the invention a tissue region of a cancer biopsy tissue sample is sliced into neighboring tissue slides resulting in respective tissue slides.

The tissue slices may be marked by single or multiple stains for the identification of respective biological features. A digital image is acquired from each of the marked tissue slices by means of an image sensor that has a number of color channels, such as an RGB image sensor.

Embodiments of the present invention are particularly advantageous due to the limitation of the scoring to the tumor or hotspot regions within the images. This way a surprisingly reliable result is obtained from the statistical model which enables to predict whether the administration of adjuvant chemotherapy is required for a given patient for the prevention of cancer reoccurrence or not. As a consequence, embodiments of the present invention provide a significant progress in the treatment of cancer patients as the unnecessary administration of chemotherapy can be avoided for those patients where the statistical model predicts a low risk of cancer reoccurrence.

An inter-marker image registration algorithm may be performed with respect to the acquired multiple digital images.

Various suitable image registration algorithms that are as such known from the prior art can be used for performing the image registration. In particular, an affine or deformable transformation can be utilized to perform the image registration.

The image registration algorithm generates a geometrical transformation that aligns corresponding points of the images. The geometrical transformation can be provided in the form of mappings, where each mapping maps the points of one of the images to corresponding points of another one of the images.

The images are aligned in accordance with the image registration. In other words, the geometrical transformations that are generated by the image registration algorithm are applied to the images for aligning the images such as to display the aligned images on a display in a two-dimensional plane.

In accordance with embodiments of the invention at least one of the tissue slices is marked by multiple stains for the acquisition of a multi-channel image. The multi-channel image is unmixed to provide a set of unmixed images. The unmixed images do not need to be registered with respect to each other or with respect to the multi-channel image as they are all based on the identical dataset that is acquired by the optical sensor from one of the tissue slices. The multi-channel image is selected as a reference image for performing the image registration algorithm with respect to the multiple images excluding the set of unmixed images. This provides a mapping of each one of the multiple images to the reference image, except for the unmixed images.

Using the multi-channel image as a reference image for the image registration is advantageous as it reduces the computational cost of performing the image registration and the alignment of the images as no image registration and alignment is required for the unmixed images.

Prognosis of hormone-positive early-stage breast cancer patients offers the opportunity to make more informed follow-up choices, for example the addition of adjuvant chemotherapy. Traditionally, pathologists have prognosticated these cancers using conventional staging, tumor proliferation index, and a small set of morphological features (gland formation, nuclear grade, and mitosis) that are manually scored from H&E slides.

Surprisingly embodiments of the invention enable to predict whether a given patient belongs to a low risk group such that e.g. hormone therapy alone is sufficient and chemotherapy and its adverse side-effects can be avoided.

It is to be noted that in the prior art an adjuvant chemotherapy is always administered to breast cancer patients in addition to hormone therapy as about 15% of breast cancer patients are not responsive to hormone therapy. As there is no way in the prior art to reliably predict whether a patient belongs to a low or high risk group, chemotherapy is always given as an adjuvant therapy. Thus, the present invention greatly reduces unnecessary hardship experienced by cancer patients as embodiments of the invention enable to identify those patients that actually do require chemotherapy such that administration of chemotherapy can be avoided for the majority of patients.

DETAILED DESCRIPTION OF THE SUBJECT DISCLOSURE

Figure 1:
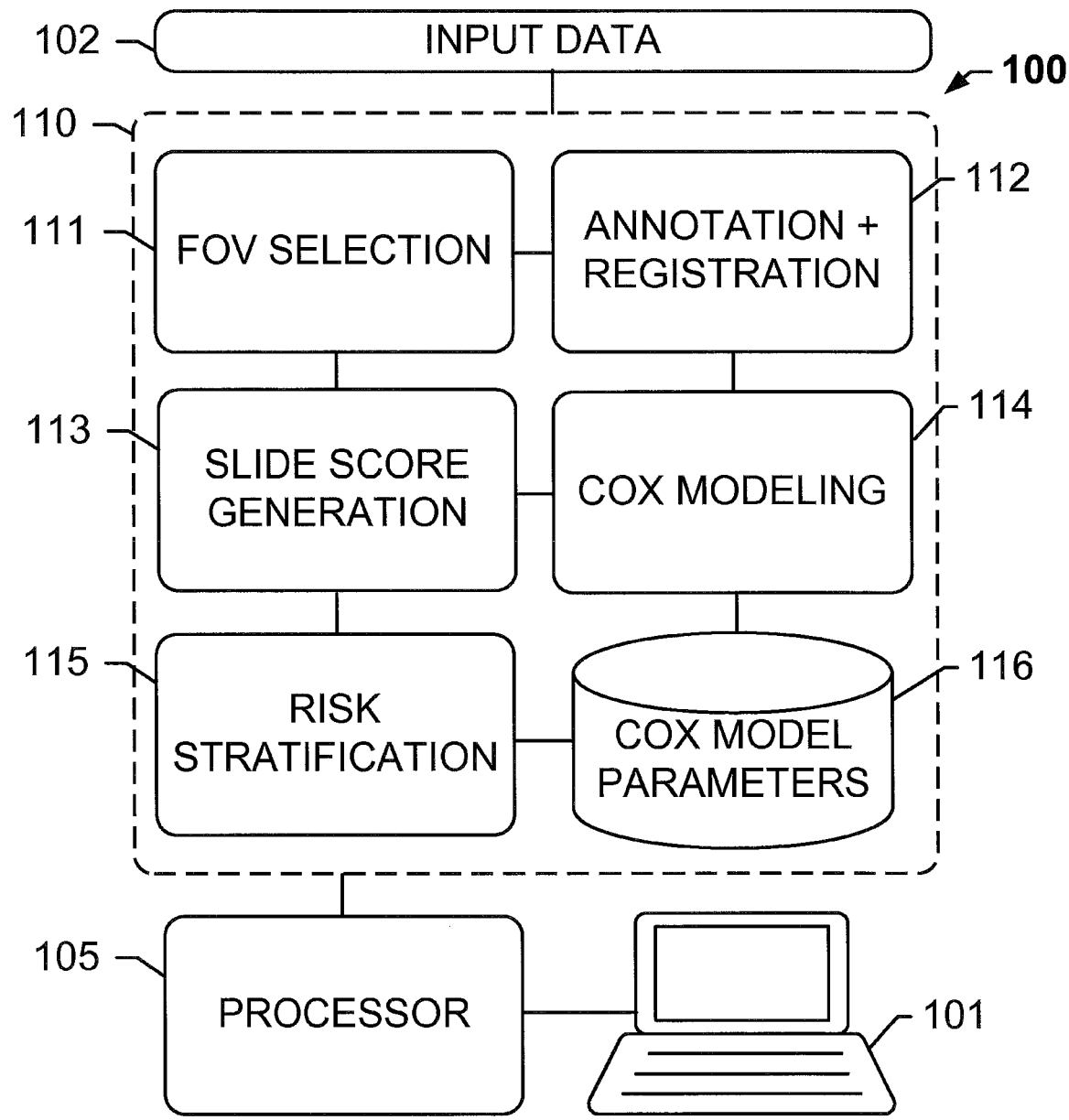
FIG. 1 shows a system for early-stage prognosis, according to an exemplary embodiment of the subject disclosure.

The subject disclosure presents systems and computer-implemented methods for providing reliable risk stratification for early-stage breast cancer patients by providing a prognostic model to predict a recurrence risk of the patient and to categorize the patient into a high or low risk group. A risk stratification system may be trained using training data that includes tissue slides from several patients along with survival data for said patients. The tissue slides may represent the time of diagnosis of the patient. The tissue slides may be processed according to a specific staining protocol and stains or biomarkers may be scored using a specific scoring protocol. For example, a series of histopathological simplex and/or multiplex tissue slides from serial sections of cancerous tissue block corresponding to each patient and stained with H&E and multiple IHC tumor and immune markers (such as tumor markers ER, PR, Ki67, HER2, etc. and/or immune markers such as CD3, CD8, CD4 etc.) are digitized using a digital pathology scanning system, for example, on a whole slide scanner or a digital microscope.

As part of IHC image analysis, the tumorous regions in each of the tumor marker IHC tissue slide are automatically analyzed and scored using relevant marker-specific image analysis algorithms to calculate scores for each marker (representing percent positivity, H-score etc.). The tumorous regions annotated to generate the slide scores may either be whole tumor regions or a specified set of regions on the digital slide. These regions can be either manually annotated by a qualified reader using a digital slide reviewing software application or automatically generated.

The risk stratification system may include a proportional hazards regression module that is used to combine the individual whole slide scores from chosen subset of all the analyzed whole slides to generate a particular risk stratification scoring algorithm. Exemplary risk stratification algorithms may include IHC3, IHC4, IHCn etc. For IHC3, only the scores from the ER, PR and Ki67 slides are used. For IHC4, slides scores from ER, PR, Ki67 and HER2 slides are used. Generically, IHCn refer to using cores from n slides. However, the overall workflow and approach to derive the risk stratification algorithm is same. The proportional hazards regression module may include a Cox proportional hazards model that is fitted to the survival data to generate a risk scoring algorithm such as an IHC3 score. Given the recurrent and non-recurrent patient data comprising tissue slides and the associated outcome information (such as recurrence free survival, overall survival etc.) along with the relevant slide level scores computed for these datasets, the proportional hazards regression model is fit to the survival data of the entire patient population and the optimal cutoff-point defined on the fitted prognostic model estimate is generated and used to stratify the patient population into low or high risk groups.

Subsequently, any single patient's tissue slides that are processed using the same staining protocol and/or image analysis methods and scoring protocol may be analyzed using the risk scoring algorithm generated during the training process, and stratified using the generated cutoff point to determine the survival probability and/or prognosis for the single patient. The same set of histopathological slides corresponding to the patient tissue are used for analysis. As with the training dataset, the same set of image analysis algorithms and tools are used to analyze and output the required set of slide level scores from the patient individual marker tissue slides to compute the risk stratification score. These scores are input into the prognostic model to predict the risk of recurrence and to stratify the patient into a low or high risk of recurrence group.

FIG. 1 shows a system for early-stage prognosis, according to an exemplary embodiment of the subject disclosure. System 100 comprises a memory 110, which stores a plurality of processing modules or logical instructions that are executed by processor 105 coupled to computer 101. Besides processor 105 and memory 110, computer 101 also includes user input and output devices such as a keyboard, mouse, stylus, and a display/touchscreen. As will be explained in the following discussion, processor 105 executes logical instructions stored on memory 110, performing image analysis and other quantitative operations resulting in an output of results to a user operating computer 101 or via a network.

For instance, input data 102 may provide a means for inputting image data from one or more scanned IHC slides to memory 110. Image data may include data related to color channels or color wavelength channels, as well as details regarding a staining and/or imaging process. For instance, a tissue section may require staining by means of application of a staining assay containing one or more different biomarkers associated with chromogenic stains for brightfield imaging or fluorophores for fluorescence imaging. Staining assays can use chromogenic stains for brightfield imaging, organic fluorophores, quantum dots, or organic fluorophores together with quantum dots for fluorescence imaging, or any other combination of stains, biomarkers, and viewing or imaging devices. Example biomarkers include biomarkers for estrogen receptors (ER), human epidermal growth factor receptors 2 (HER2), Ki-67, and progesterone receptors (PR), wherein the tissue section is detectably labeled with antibodies for each of ER, HER2, Ki-67 and PR. In some embodiments of the subject disclosure, the operations of scoring, cox modeling, and risk stratification are depending on the type of biomarker being used as well as the field-of-view (FOV) selection and annotations. Therefore, any other biomarker tissue slides (like immune markers or some other additional markers) will trigger slide image analysis and scoring specific to the particular marker and include those scores in the Cox model fitting process.

Once the image data is received, an image in a series of images corresponding to slides comprising serial tissue sections may be displayed on a user interface on terminal 101 or remotely. For example, a user interface may be provided by a field-of-view (FOV) selection module 111 that enables selection of a region of an IHC image for further analysis by the other modules. A pathologist operating the terminal may select the FOV using the user interface. Several FOV selection mechanisms may be provided, such as designating known or irregular shapes, or defining an anatomic region of interest (e.g., tumor region). In one example, the field of view is a whole-tumor region selected on an IHC image stained with an H&E stain combination. The FOV selection may be performed by a pathologist or by automated image-analysis algorithms, such as tumor region segmentation on an H&E tissue slide, etc. For example, a user may select that the FOV as the whole slide or the whole tumor, or the whole slide or whole tumor region may be automatically designated as the FOV. As will be explained herein the FOV selection determines which annotation, scoring, modeling, and stratification method is used.

Annotation and Registration module 112 annotates the FOV on the first slide and maps the annotations across the remainder of the slides. As described herein, several methods for annotation and registration are possible, depending on the defined FOV. For example, a whole tumor region annotated on a Hematoxylin and Eosin (H&E) slide from among the plurality of serial slides may be selected automatically or by a pathologist on an interface such as VIRTUOSO/VERSO™ or similar. Since the other tissue slides correspond to serial sections from the same tissue block, the annotation and registration module 112 executes an inter-marker registration operation to map and transfer the whole tumor annotations from the H&E slide to each of the remaining IHC slides in the series. Exemplary methods for inter-marker registration are described in further detail in commonly-assigned and co-pending application WO2014140070A2, "Whole slide image registration and cross-image annotation devices, systems and methods", filed Mar. 12, 2014, the contents of which are hereby incorporated by reference in their entirety herein. In some embodiments, any other method for image registration and generating whole-tumor annotations may be used. For example, a qualified reader such as a pathologist may annotate a whole-tumor region on any other IHC slide, and execute registration module 112 to map the whole tumor annotations on the other digitized slides. For example, a pathologist (or automatic detection algorithm) may annotate a whole-tumor region on an H&E slide triggering an analysis of all adjacent serial sectioned IHC slides to determine whole-slide tumor scores for the annotated regions on all slides.

An alternate means for FOV selection 111 and registration 112 comprises detecting or specifying representative regions or "hot spots" on a Ki67 digitized whole slide. Specific regions of the whole slide that contain relatively high and heterogeneous amounts of Ki67 protein may selected, for instance in a rectangular shape or any other shape. FOV selection module 111 may enable a manually drawn selection, or automated image analysis algorithms may highlight such regions on a Ki67 slide. An inter-marker registration operation may be used to map these "hot spots" to equivalent annotated regions on the other IHC slides. For example, the other slides may include H&E, ER, PR, and/or HER2 tissue slides. A heat map may be generated given annotations on a first slide, such as a Ki67 slide, and regions in the heat map which are locally dominant may be considered to be hot spots, possibly which a qualified reader such as a pathologist considers to be important. Visually, the heat map presents a high-level overview of the scoring metric of interest. For instance, a heat map of a Ki67 slide is indicative of the percent positivity in the tumor region, and used to generate the FOV that is registered on adjacent IHC slides. In either case, whether the whole tumor or only "hot spots" are annotated, the corresponding regions on the remaining slides necessarily or likely correspond to similar tissue types, assuming the magnification remains constant across the series. Moreover, the varying fields of view result in different scores for each slide and for the whole-slide score, such as IHC3, IHC4, or IHCn as further described herein. Exemplary methods of hot spot detection are described in PCT/EP2015/062015, entitled "An Image Processing Method and System for Analyzing a Multi-Channel Image Obtained From a Biological Tissue Sample Being Stained By Multiple Stains, filed May 29, 2015, the contents of which is hereby incorporated by reference in its entirety.

Image analysis algorithms may be used to determine a presence of one or more of a nucleus, a cell wall, a tumor cell, or other structures within the field of view. Stain intensity values and counts of specific nuclei for each field of view may be used to determine a percent positivity, H-Score or a regional heterogeneity. This data is used to determine a score for each slide by slide score generation module 113. For example, automated image analysis algorithms interpret each one of the IHC slides in the series to detect tumor nuclei that are positively and negatively stained for a particular biomarker, such as Ki67, ER, PR, HER2, etc. Based on the detected positive and negative tumor nuclei, various slide level scores such as marker percent positivity, H-scores, regional heterogeneity, etc. may be computed using one or more of a plurality of methods. In exemplary embodiments, the automated analysis of tissue slides use the assignee VENTANA's FDA-cleared 510(k) approved algorithms. Alternatively or in addition, any other automated algorithms may be used to analyze selected regions and generate scores. In some embodiments, scores are manually input into the system prior to whole-slide scores being generated. Exemplary methods for scoring are described in further detail in commonly-assigned and co-pending applications WO2014102130A1 "Image analysis for breast cancer prognosis" filed Dec. 19, 2013, and WO2014140085A1 "Tissue object-based machine learning system for automated scoring of digital whole slides", filed Mar. 12, 2104, the contents of each of which are hereby incorporated by reference in their entirety herein.

The resulting slide-level scores computed by scoring module 113 are combined together to generate either IHC3 or IHC4 scores for the series of slides. IHC3 or IHC4 refers to the number of marker slides that are being used to generate the combined score. For example an IHC3 score is computed for slides scored using ER, PR, and Ki67 scores, while an IHC4 score is computed for slides scored with ER, PR, Ki67, and HER2 scores. For additional marker tissue slides (H&E, tumor or immune markers) included in the scoring may be represented as IHCn, where n is the number of marker slide scores that are used to generate the overall combined score. Either IHC3, IHC4, or IHCn scores may be based on a whole-tumor FOV selection or a "hot spot" FOV selection for Ki67 markers, as described herein. The scores may be based on heterogeneity and/or H-score in addition to the whole-tumor percent positivity score for each slide.

For example, the H-score may be computed from the binned intensity values for positively stained tumor nuclei. Heterogeneity refers to tumor regional heterogeneity—which quantifies the variability of the percent positivity and H-score across the whole tumor region.

The scores computed from individual marker slides may then be integrated to determine a risk score (for example, IHC3) using statistical methodology that includes fitting with a Cox proportional hazards regression model as performed by Cox modeling module 114. For example, the IHC3 or IHC4 combination scores and the combined heterogeneity scores are entered into a Cox proportional hazards regression model to maximize the combined predictive capabilities of both measures. The Cox proportional hazards regression method models the impact of explanatory variables (such as individual marker whole slide scores) on the survival probability time to distant recurrence by taking two linear variables and finding the best logistic regression model of the two to predict time to distant recurrence.

More details regarding the use of Cox modeling to predict cancer recurrence may be found in Prognostic Value of a Combined Estrogen Receptor, Progesterone Receptor, Ki-67, and Human Epidermal Growth Factor Receptor 2 Immunohistochemical Score and Comparison With the Genomic Health Recurrence Score in Early Breast Cancer, Jack Cuzick, Mitch Dowsett, Silvia Pineda, Christopher Wale, Janine Salter, Emma Quinn, Lila Zabaglo, Elizabeth Mallon, Andrew R. Green, Ian O. Ellis, Anthony Howell, Aman U. Buzdar, and John F. Forbes Journal of Clinical Oncology 2011 29:32, 4273-4278, the contents of which are hereby fully incorporated by reference herein in their entirety.

In this embodiment, Cox modeling module 114 may be trained by comparing the biomarker/IHC scores for individual slides with survival data comprising populations of high and low risks to determine whole-slide scoring algorithms depending on the type of FOV selection and annotation/registration being used. A cutoff point is determined that matches the input survival data, using a log-rank-test statistic to determine an accurate prediction of low and high risk. The scoring algorithms and cutoff points generated during training may be used to analyze new patient slides and provide a risk assessment or prognosis via risk stratification module 115. As described herein, in some embodiments of the subject disclosure, the operations of scoring 113, cox modeling 114, and risk stratification 115 are dependent on the type of biomarker being used as well as the field-of-view (FOV) selection and annotations. Therefore, any other biomarker tissue slides (like immune markers or some other additional markers) will trigger slide scoring specific to the particular marker and include those scores in the Cox model fitting process and use them. Similarly, if any additional slide scoring metric from an H&E slide or any other slide may be added as a variable in an IHC(x) equation and the appropriate Cox model may be derived for that combination. The parameters for each workflow (wherein a workflow comprises a FOV selection and annotation+registration protocol) may be stored in cox model parameters database 116.

As described herein, the coefficients for determining the whole-slide scores may be determined based on training cohort. Briefly, a plurality of training images along with actual survival data for the patients associated with the training images are input into system 100. The slides represent patients with Stage 1 and 2 cancer, and include ER Positive and HER2 negative tissue slides. The slide series are scored, and the Cox model is statistically fit with the individual slide scores including ER10, PR10, log (1+Ki67 percent positivity) and HER2 binary scores as variable data. For either the whole-tumor workflow or for the "hot spot" workflow both IHC3 and IHC4 models are derived based on the comparison of the actual survival data with the predicted model, for instance, by using a log-rank-test. The typical equation is represented as:

$$IHC3\_Score = a*ER10 + b*PR10 + c*\log(1+Ki67\_PercentPositivity)$$

Coefficients a, b, and c may be fitted based on the training data to ensure that the prediction matches the survival data, as further described herein, and may be stored in parameter database 116.

Similarly the IHC4 equation may be represented as:

$$IHC4\_Score = p*ER10 + q*PR10 + r*\log(1+Ki67\_PercentPositivity) + s*HER2\_score$$

The coefficients p, q, r, and s also vary depending on the workflow (whole-tumor versus hot spot selection), and are stored in the parameter database. The newly-derived constants may be retrieved in test cases following a specific workflow and to apply the optimal cutoff point for determining accurate survival for that particular workflow to stratify the scores into low-risk and high-risk groups for cancer recurrence, rather than succumb to errors or unreliable predictions caused by using standard methods described in the prior art. Similar methods may be used to derive specific formulae/coefficients when a tumor regional heterogeneity metric is combined as an additional variable input into the Cox model fitting operation. Therefore, the adjustments may be performed for any combination of considered marker slides and metrics, and may be adapted or "trained" for any type of workflow (combination of staining, FOV selection, annotation, registration), thereby providing reliable predictions for subsequent test slides following the same workflow. In other words, training the system with existing survival data for a specific workflow enables building of a prognostic model to be applied to new patient slides in a clinical context.

For instance, in a clinical or diagnostic workflow, when a new slide series comprising H&E and IHC slides from a new patient is input into system 100, and annotations generated and FOVs analyzed using image analysis algorithms to output scores, the corresponding IHC3/IHC4 formulae with specific coefficients are used to compute the whole-slide score for that patient. If whole tumor annotations are performed, WholeTumor_IHC3 and WholeTumor_IHC4 scores may be computed. If "hot spot" annotations are performed, Ki67_HotspotBased_IHC3 and Ki67_HotspotBased_IHC4 scores may be computed. The cutoff points for these scores are used to provide a prognosis for the patient, i.e. stratifying their risk group, based on the cutoff points generated during comparisons of training data with survival curves.

As described above, the modules include logic that is executed by processor 105. "Logic", as used herein and throughout this disclosure, refers to any information having the form of instruction signals and/or data that may be applied to affect the operation of a processor. Software is one example of such logic. Examples of processors are computer processors (processing units), microprocessors, digital signal processors, controllers and microcontrollers, etc. Logic may be formed from signals stored on a computer-readable medium such as memory 110 that, in an exemplary embodiment, may be a random access memory (RAM), read-only memories (ROM), erasable/electrically erasable programmable read-only memories (EPROMS/EEPROMS), flash memories, etc. Logic may also comprise digital and/or analog hardware circuits, for example, hardware circuits comprising logical AND, OR, XOR, NAND, NOR, and other logical operations. Logic may be formed from combinations of software and hardware. On a network, logic may be programmed on a server, or a complex of servers. A particular logic unit is not limited to a single logical location on the network. Moreover, the modules need not be executed in any specific order.

Figure 2A:
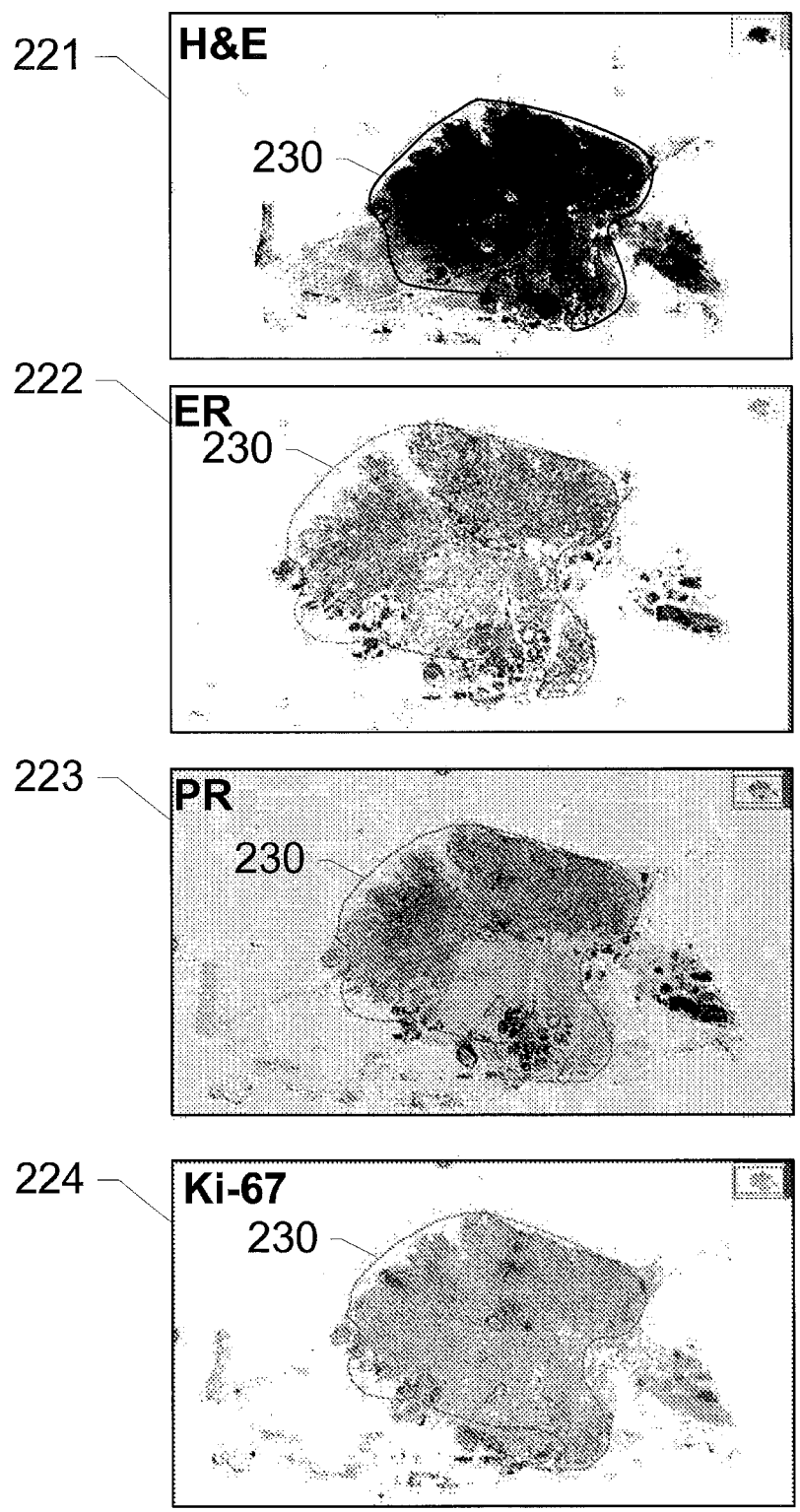
FIGS. 2A and 2B show different fields of view for an annotated and registered slide series, according to exemplary embodiments of the subject disclosure.
Figure 2B:
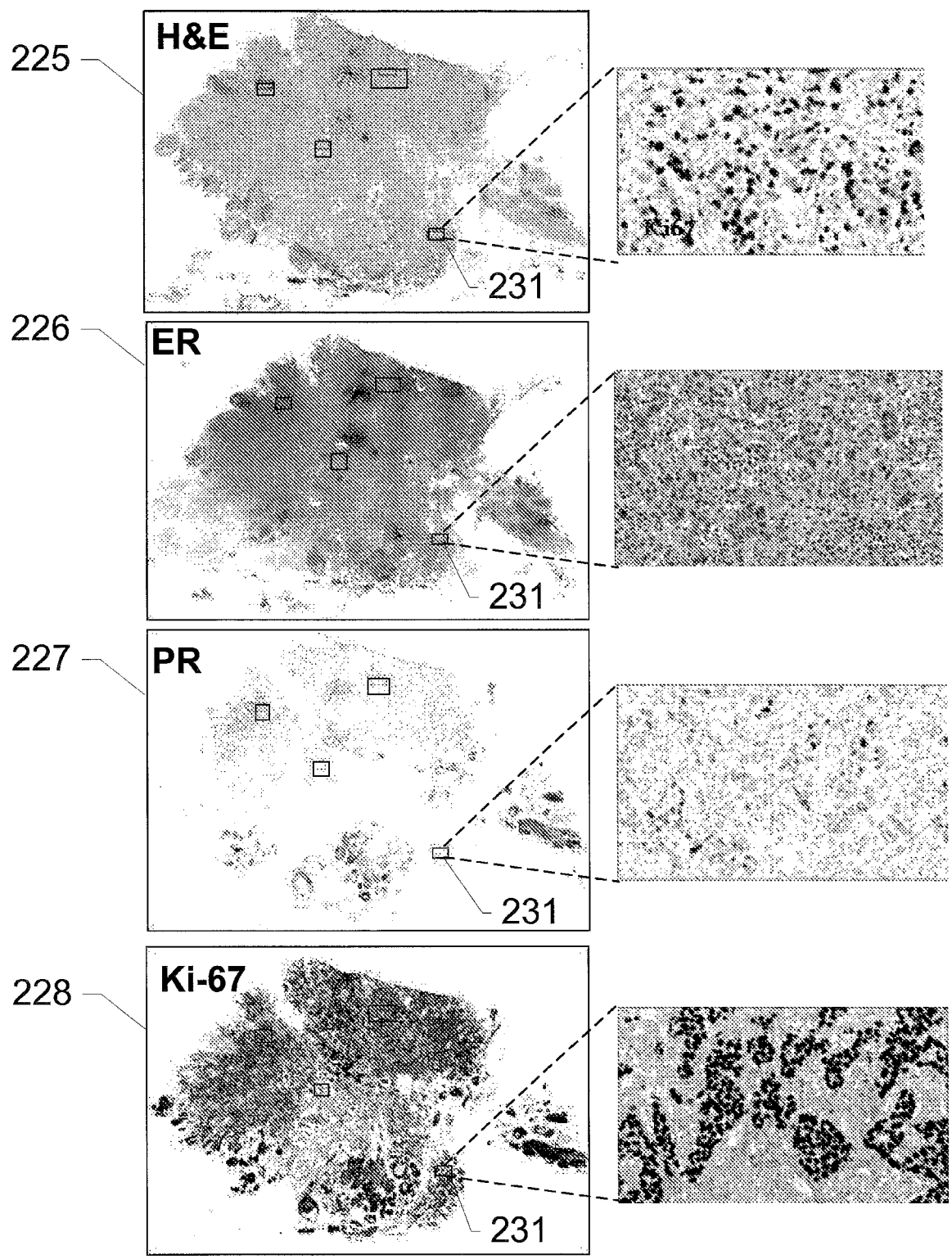

FIGS. 2A and 2B show different fields of view for an annotated and registered slide series, according to exemplary embodiments of the subject disclosure. As described above, an image in a series of images corresponding to slides comprising serial tissue sections may be displayed on a user interface. FIG. 2A shows a series of images of serial tissue sections, according to an exemplary embodiment of the subject disclosure. For example, adjacent tissue sections may be stained with H&E, ER, PR, and Ki-67, respectively, and the corresponding images 221, 222, 223, and 224 may be depicted on a user interface such as VIRTUOSO™ interface or similar interface for enabling selection of a field of view (FOV) 230. The FOV 230 may comprise a region of one of the images, for example a tumor region. A pathologist may select the FOV using the user interface, or automated FOV selection mechanisms may be used based on feature detection or other image analysis operations. In this embodiment, the field of view 230 is a whole slide or whole tumor region. FOV 230 is initially annotated on the H&E image 221, and since the other tissue slides correspond to serial sections from the same tissue block, the inter-marker registration module maps and transfers the whole tumor annotations from the H&E slide 221 to each of the remaining IHC slides 222, 223, and 224.

FIG. 2B shows an alternate means for FOV selection using representative regions or "hot spots" 231 on a Ki67 digitized whole slide 225. Hot spots are specific regions of the whole slide that contain relatively high and heterogeneous amounts of Ki67 protein. The FOV 231 may, for instance, be in the form of a rectangular shape 231. Other embodiments may provide a manually drawn FOV selection, or automated image analysis algorithms may highlight such FOV regions on the Ki67 slide 225. An inter-marker registration operation as described above may be used to map these "hot spots" to equivalent annotated regions on the other IHC slides such as ER 226, PR 227, and H&E slide 228. Shown on the right hand side of FIG. 2B are the zoomed-in versions of these hot spots, depicted at 20× magnification. Additional IHC slides are not depicted by FIG. 2B or 2A may be similarly annotated, such as HER2. In either case, whether the whole tumor or only "hot spots" are annotated, the corresponding regions on the remaining slides necessarily correspond to similar tissue types, assuming the magnification remains constant across the series.

Figure 3:
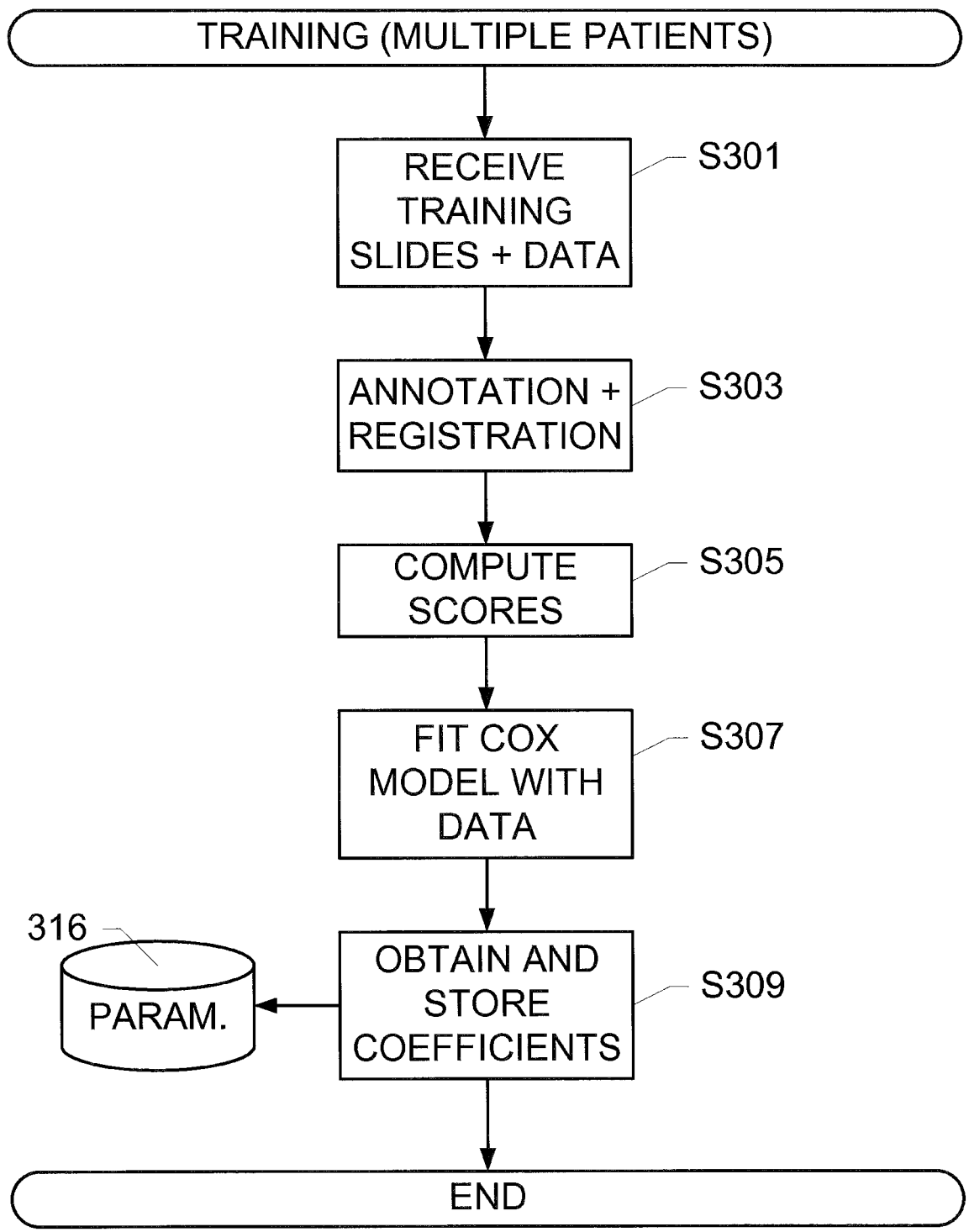
FIG. 3 shows a method for training an early-stage prognosis system, according to an exemplary embodiment of the subject disclosure.
Figure 5:
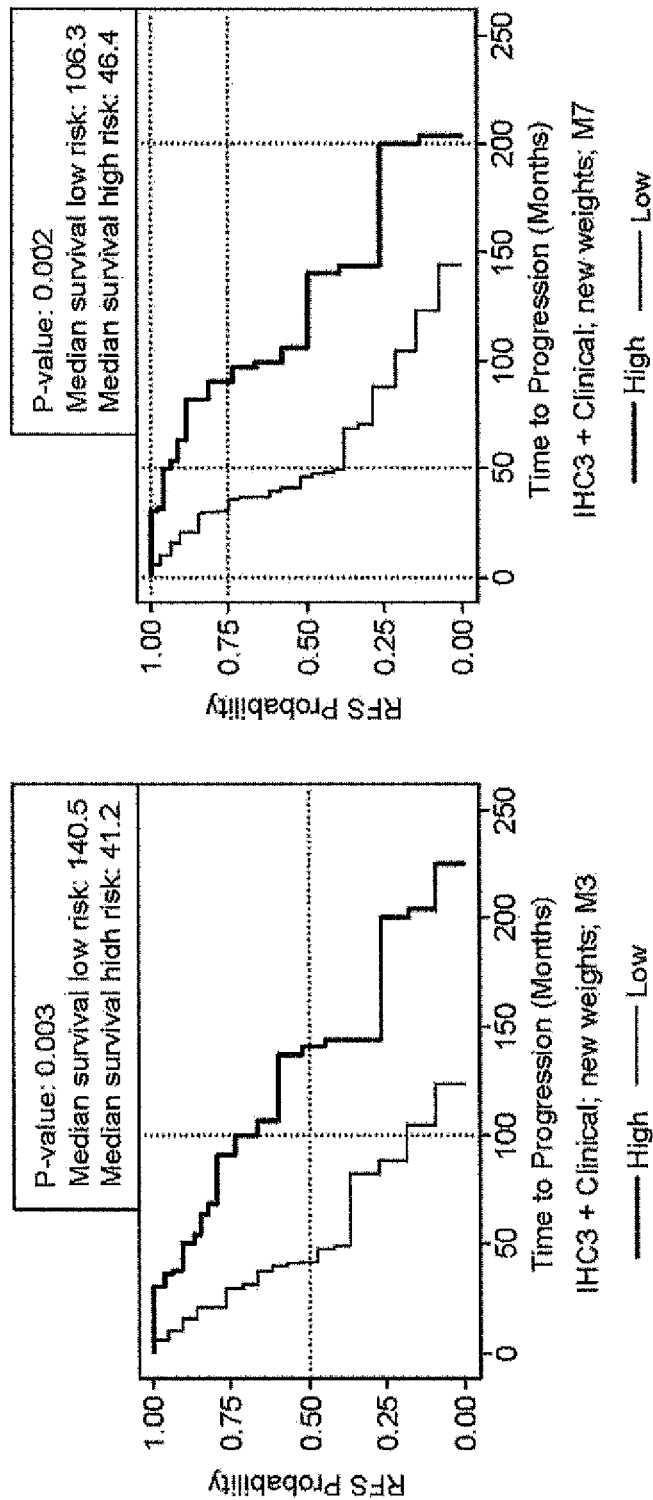
FIGS. 5A and 5B show exemplary survival curves.

FIG. 3 shows a method for training an early-stage prognosis system, according to an exemplary embodiment of the subject disclosure. For instance, an imaging system or other means of input may provide image data from one or more series of training IHC slides a system as described herein, with the system receiving the training slides and image data (S301). Image data is comprised of images of tissue sections from a plurality of patients in order to train the system, and may include color channels or frequency channels, tissue and biomarker data, as well as additional data or metadata identifying one or more clinical outcomes for the patients associated with the tissue sections. The clinical outcomes include, for instance, how long the patients survived, whether or not the cancer recurred, etc. The clinical outcome may include generating survival curves from the patient survival outcome data, the patients, comprising data points compiled over a specified period, such as 10 or 20 years. For example, Kaplan-Meier survival curves may be estimated. In one example embodiment, a training cohort of 120 series of slides representing 120 breast-cancer patients, a representative pool of patients in whom the cancer has recurred and not recurred, at 5 slides per series, along with the information about how long they survived and if and when the cancer has recurred from the date of initial diagnosis were provided. FIG. 5 depicts the estimated exemplary Kaplan-Meier survival curves for the recurrent and non-recurrent patient groups. Additional information provided may include any information related to the staining platform, including a concentration of chemicals used in staining, a reaction times for chemicals applied to the tissue in staining, and/or pre-analytic conditions of the tissue, such as a tissue age, a fixation method, a duration, how the section was embedded, cut, etc.

Annotation and registration operations (S303) may be performed on the input training slides. Fields of view (FOVs) based on different workflows such as whole-tumor annotation or Ki-67 hotspot annotation may be selected for registration, as further described herein. For example, a first image in the series may be displayed on a user interface for enabling a FOV selection of the first image, either by a pathologist, or automatically using feature detection algorithms. A whole tumor region may be annotated on an H&E slide, or hot spots may be identified and annotated on a Ki67 digitized whole slide. An inter-marker registration operation may be used to map and transfer the whole tumor annotations from the first slide to each of the remaining slides in the series.

Each series may be scored and a risk computed (S305) using the methods described herein. For instance, an IHC3 score for 3 markers (ER, PR, Ki67) may be computed, and heterogeneity scores may be included. These scores are fitted (S307) to a Cox proportional hazards regression model along with the survival data in order to generate a whole-slide scoring algorithm to be applied to test cases (see FIG. 4). For instance the model may be fitted with the event information in the survival curves for the particular training patient. The fitting (S307) includes determining whether or not the fitted prognostic model shows discrimination between recurrence and no recurrence. For either the whole-tumor workflow or for the "hot spot" workflow, both IHC3 and IHC4 models are derived based on the comparison (S307) of the actual survival data with the predicted model. The equation can be written as:

$$IHC3\_Score = a*ER10 + b*PR10 + c*\log(1 + 10*Ki67\_PercentPositivity)$$

Coefficients a, b, and c may be obtained (S309) based on the fitting of the training data to the Cox model to ensure that the prediction matches the survival data. For example, the some embodiments generate values represented as:

$$IHC3 = 93.1*[-0.086\ ER10 - 0.081*PR10 + 0.281*\log(1 + 10*Ki67)]$$

In this case, 93.1 is a shrinkage parameter that is used to shrink the weights to account for model overfitting. The Cox model coefficients a, b, c, etc. may be stored (S309) in parameters database 316. Therefore, the equations may be considered optimized, and stored for clinical use, for instance while performing testing operations listed in FIG. 4.

Table 1 shows a plurality of optimized coefficients for different weights for each workflow, based on an experimental embodiment of the subject disclosure.

TABLE 1

| Annotation | No Shrinkage Parameter | | Shrinkage Parameter Applied | |
|---|---|---|---|---|
| | Whole-Tumor Coefficient (se) | Ki67 Hot Spot Coefficient (se) | Whole-Tumor Coefficient (se) | Ki67 Hot Spot Coefficient (se) |
| ER Score | −2.45 (10.55) | −3.27 (8.77) | −1.17 (5.03) | −1.75 (4.68) |
| PR Score | −11.02 (6.38) | −6.71 (5.69) | −5.26 (3.04) | −3.58 (3.04) |
| Ki67 Score | 4.73 (2.04) | 5.12 (1.62) | 2.26 (0.97) | 2.73 (0.86) |

These values are merely exemplary, and persons having ordinary skill in the art will realized upon reading this disclosure that the adjustments to the coefficients may be performed for any combination of the included marker slides and associated metrics, and may be adapted or "trained" for any type of workflow, while continuing to provide reliable predictions for subsequent test slides following the same workflow. In other words, fitting the Cox model with existing survival data for a specific tissue sample data and workflow enables building of a prognostic model to be applied to new patient slides in a clinical context.

Figure 4:
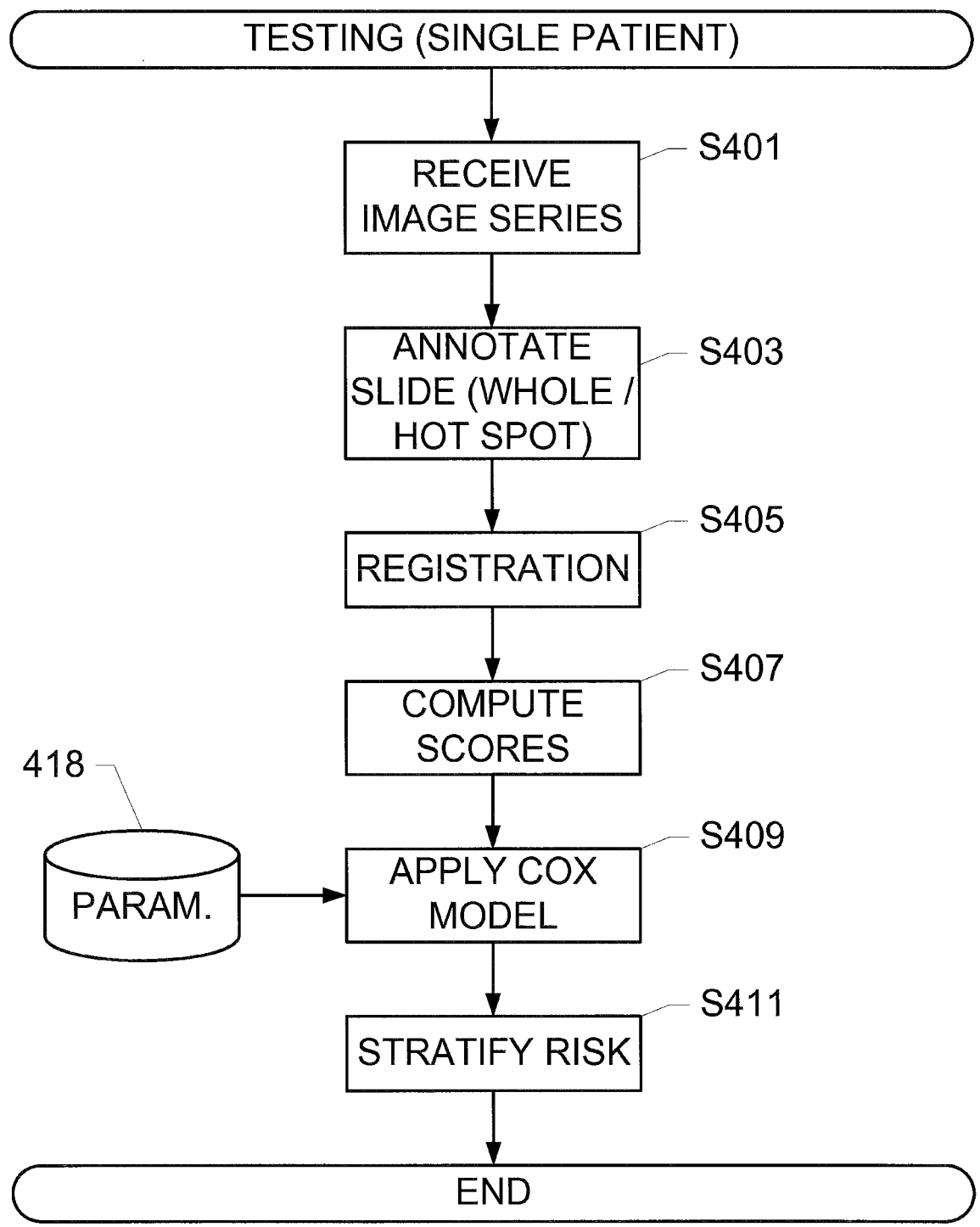
FIG. 4 shows a method for early-stage prognosis, according to an exemplary embodiment of the subject disclosure.

FIG. 4 shows a method for early-stage prognosis, according to an exemplary embodiment of the subject disclosure. This method may use components described with reference to system 100, or other components that perform similar functions. For instance, an image series corresponding to a single patient undergoing diagnosis may be received (S401) from an imaging system or any other input. The image series may include data in the form of color channels or frequency channels representing serial sections of tissue stained with various biomarkers. Example biomarkers include biomarkers for estrogen receptors (ER), human epidermal growth factor receptors 2 (HER2), Ki-67, and progesterone receptors (PR). The imaging system may include the ISCAN COREO™ product of the assignee Ventana Medical Systems, Inc. The image data corresponds to cancerous or significantly cancerous sections retrieved from a single patient.

Once the image data is received (S401), an image in a series of images corresponding to slides comprising serial tissue sections may be displayed on a user interface for field-of-view (FOV) selection and annotation (S403). Several annotation mechanisms (S403) may be provided, such as designating known or irregular shapes, or defining an anatomic region of interest (e.g., tumor region). In one example, the field of view is a whole slide, whole tumor region, or whole tissue section. The annotation (S403) annotates the FOV on the first slide and a registration operation (S405) maps the annotations across the remainder of the slides. As described herein, several methods for annotation and registration may be utilized, depending on the defined FOV. For example, a whole tumor region on a Hematoxylin and Eosin (H&E) slide from among the plurality of serial slides may be defined, and registration operation (S405) maps and transfers the whole tumor annotations from the H&E slide to each of the remaining IHC slides in the series. Alternatively, representative regions or "hot spots" may be identified on a Ki67 digitized whole slide, and may be mapped to equivalent annotated regions on the other IHC slides.

Given the FOV, image analysis operations are used to compute scores (S407) for each slide. The scores for each slide may be based on a determination of a percent positivity, as well as a regional heterogeneity. Tumor nuclei that are positively and negatively stained for a particular biomarker, such as Ki67, ER, PR, HER2, etc. are counted, and a percent positivity is computed. Additional scoring mechanisms may be employed, such as H-scores representing regional heterogeneity of a particular marker or protein. In exemplary embodiments, the automated analysis of tissue slides use the assignee VENTANA's FDA-cleared 510(k) approved algorithms. Alternatively or in addition, any other automated algorithms may be used to analyze selected regions and generate scores. The resulting slide-level scores may be combined together to generate IHC3, IHC4, or IHCn scores for the series of slides, depending on the number of individually-stained slides. Any scores computed from the H&E slide can also be included to the information from IHC slides to accordingly specify a different risk scoring metric. The scores are based on, for example, a whole-tumor FOV selection or on a "hot spot" FOV selection.

The IHC3 or IHC4 combination scores and the combined regional heterogeneity scores may then be entered into a Cox proportional hazards regression model (S409) to maximize the combined predictive capabilities of both measures. The Cox proportional hazards regression model models time to distant recurrence by taking two variables and finding the best logistic combination of the two to predict time to distant recurrence. Depending upon the type of FOV selected, a plurality of coefficients or parameters for the Cox model may be retrieved from parameter database 418. The coefficients may be based on training data for similar workflows as described with respect to FIG. 3, thereby enabling survival predictions for the slide series of the individual patient being tested. Based on the training workflow, optimized cut-off points are provided from database 418 for enabling the scores to be stratified (S411) into low-risk and high-risk groups for cancer recurrence besides medical applications such as anatomical or clinical pathology, prostrate/lung cancer diagnosis, etc., the same methods may be performed to analysis other types of samples such as remote sensing of geologic or astronomical data, etc. The operations disclosed herein may be ported into a hardware graphics processing unit (GPU), enabling a multi-threaded parallel implementation.

Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices. Examples of input devices include a keyboard, a cursor control devices (e.g., a mouse), a microphone, a scanner, and so forth. Examples of output devices include a display device (e.g., a monitor or projector), speakers, a printer, a network card, and so forth. Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provide one or more graphical representations to a user. Interfaces are typically enabled to accept user inputs using means of selection or input known to those of ordinary skill in the related art. The interface may also be a touch screen device. In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof. A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows type operating system from the Microsoft Corporation; the Mac OS X operating system from Apple Computer Corp.; a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices that can be used to store the desired information and that can be accessed by a computer. Computer readable storage media may include volatile and non-volatile, removable and non-removable media implemented in any method or technology for storage of information such as computer readable instructions, data structures, program modules, or other data. Examples include any commonly available random access memory (RAM), read-only memory (ROM), electronically erasable programmable read-only memory (EEPROM), digital versatile disks (DVD), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device. In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts. Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications. As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor, in a known manner into system memory, or cache memory, or both, as advantageous for execution. Also, a computer may include one or more library files, experiment data files, and an internet client stored in system memory. For example, experiment data could include data related to one or more experiments or assays, such as detected signal values, or other values associated with one or more sequencing by synthesis (SBS) experiments or processes. Additionally, an internet client may include an application enabled to access a remote service on another computer using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

Exemplary scoring algorithms are described herein. For example, from the WO2014140085A1 application titled "Tissue object-based machine learning system for automated scoring of digital whole slides", at least some embodiments of the disclosed technology are directed to imaging systems for automatically interpreting and scoring tissue specimen slides, for example, specimens stained with an immunohistochemical (IHC) assay. The system analyzes a region of an image or an entire image (e.g., a digital whole-slide image), based at least in part on information and characteristics associated with the whole slide and selects features for quantitative analysis. A whole slide image is considered an image of all or substantially all of the tissue containing regions (e.g., all regions of the slide excluding labels, markers, and blank areas) of a slide. The disclosed system identifies cellular structures (e.g., nuclear objects, nuclei seed) and cells in a region of a slide (e.g., a particular tissue region of the slide) or the whole slide, based at least in part on information pertaining to data associated with tissue containing regions of the slide. Furthermore, the disclosed system may count cells, compute various types of local and global features of these cells, identify the cell types, and perform quantitative analysis. The feature computation can use information from not only an annotated region of a slide but also information from the whole slide (e.g., tissue-containing regions of the slide analyzed at multiple magnifications). The system can automatically count and classify cells and score the image and/or entire slide based at least in part on selected fields of view and/or the whole slide based at least in part on information or data associated with the whole slide (i.e., all of the tissue containing regions of the slide). The score can be used for slide interpretation. For example, the system can accurately count nuclear objects to determine information about the tissue to assist with reliable and reproducible slide interpretation. In one embodiment, the system counts positively-stained nuclear objects and/or negatively-stained nuclear objects to score, for example, a biological specimen (e.g., tumor tissue). In some embodiments, an overlay image is produced to label features of interest in the image of a specimen from a subject. Scoring of the tissue may be performed to predict and/or generate a prognosis for the tissue sample. In some embodiments, a pathologist can approve or reject a slide score. If the slide score is rejected, the automated score can be replaced with a manual score (e.g., a score based at least in part on visual inspection). The system can have a classifier that was trained based at least in part on a set of training or reference slides for each marker, for example a biomarker. The set of training slides for a marker can represent all desired data variability. Different sets of slides can be used to train a classifier for each marker. Accordingly, for a single marker, a single classifier is obtained after training. Since there is variability between the image data obtained from different markers, a different classifier can be trained for each different biomarker so as to ensure better performance on unseen test data, where the biomarker type of the test data will be known. The trained classifier can be selected based at least in part on how best to handle training data variability, for example, in tissue type, staining protocol, and other features of interest, for slide interpretation. The system can analyze a specific region of an image based at least in part on information within that region, as well as information outside of that region. In some embodiments, a multi-stage binary classifier can identify positive and negative nuclei.

The positive nuclei can be distinguished from the negative nuclei, lymphocytes, and stroma. Additionally, the negative cells and lymphocytes can be distinguished from stroma. Lymphocytes are then distinguished from the negative nuclei. In further classification, the positive cells can be distinguished from background cells. For example, if the positive cells have brown stained nuclei, the background cells may exhibit cytoplastmic blush that can be filtered out. Based at least in part on the number of positive/negative nuclei, a score (e.g., a whole-slide score) can be determined.

In some embodiments, a method for whole-slide interpretation includes identifying portions of a digitized whole slide image corresponding to tissue.

Based at least in part on the color characteristics of the substrate (e.g., glass) on which the biological specimen (e.g., tissue) is placed the tissue and tissue regions of interest are identified. Seed points are detected for the identified tissue regions of interest, and tissue nuclei objects are extracted from the identified regions. For each of the extracted tissue objects, characteristics of the extracted object are identified, and a trained classifier can be used to classify the extracted object. The trained classifiers can be modified by a user, a physician, or the like. Different trained classifiers can be used to analyze different types of tissues and markers. A computer-readable storage medium can store data (e.g., classifiers, algorithms, etc.) and instructions that, if executed by a computing system having a processor, cause the computing system to perform such methods.

In further embodiments, a supervised learning system for classifying objects within digitized images of tissue data includes means for training a classifier based at least in part on ground truth slides, means for receiving a digitized image of tissue data associated with an input slide, and means for analyzing the digitized tissue data. The means for analyzing the digitized tissue data can comprise means for detecting potential nuclei seed points within the digitized tissue image and means for extracting objects from the digitized tissue image. In one embodiment, the system further includes means for classifying each of the extracted objects.

In some embodiments, a method used by a computing system can provide interpretation of digitized images of tissue slides, for example, IHC slides. The method includes receiving digitized images of tissue samples of reference training slides (e.g., ground truth or training slides). In some embodiments, a set of reference slides is used. For example, the reference slide images can be images of the same type of tissue as the tissue to be analyzed. The system learns about characteristics of the observed variability in the digitized image because of data variability in tissue, staining protocols, image scanning and artifacts sources based at least in part on the known information associated with the reference images. The system can receive at least one classification method and train a classifier using the digitized images of tissue samples. The classifier can be modified using additional reference slides, if needed or desired.

The system, in some embodiments, can receive a digitized image of data associated with an input slide with a sample from a subject. In some embodiments, the scoring of the slide occurs in, for example, one of two modes: a Field of View (FOV) mode and an automated mode. In the FOV mode, a user, such as a pathologist, outlines or "annotates" a number of regions (e.g., three or more regions) in a whole slide image and the analysis algorithm is performed with respect to the annotated regions. A final composite score is obtained based at least in part on the number of positive and negative tumor nuclei detected in all these annotated regions. In the automated mode, either an Area of Interest (AoI) detector finds or identifies a tissue region in the whole slide image or the tissue annotations are automatically generated by some other image analysis algorithm, such as image registration algorithm which maps annotations from the adjacent serial section to the IHC tissue slide. The tissue region is then segmented into tiles and classification and nuclei counting algorithms are performed with respect to each tile that contains tissue. Additionally, a composite score can be obtained based at least in part on the image tiles containing tissue. Though the underlying methodology for detecting, counting, and classifying cells in a given image are similar in that the image may be a user annotated region or an automatically obtained tile in the whole slide image after AoI detection, there is at least one difference in the two workflows. The FoV mode relies on manual input in terms of FOV selection while the automated mode does not. The annotated FOV mode is further discussed with respect to FIG. 2 while the automated mode is further discussed with respect to FIG. 3. One or more regions within the identified tissue are identified based at least in part on dominant colors. For identified regions, seed points within the identified region are detected, and objects from the identified regions are extracted. Features of the extracted object(s) are computed such that the trained classifier classifies the extracted object(s) based at least in part on the computed features of the extracted object. In some embodiments, a computer system can be programmed to automatically identify features in an image of a specimen based at least in part on one or more selection criteria, including criteria based at least in part on color characteristics, sample morphology (e.g., cell component morphology, cell morphology, tissue morphology, anatomical structure morphology, etc.), tissue characteristics (e.g., density, composition, or the like), spatial parameters (e.g., arrangement of tissue structures, relative positions between tissue structures, etc.), image characteristic parameters, or the like. If the features are nuclei, the selection criteria can include, without limitation, color characteristics, nuclei morphology (e.g., shape, dimensions, composition, etc.), spatial parameters (e.g., position of nuclei in cellular structure, relative position between nuclei, etc.), image characteristics, combinations thereof, or the like. After detecting candidate nuclei, algorithms can be used automatically to provide a score or information about the entire analyzed image. The selection criteria can be modified or determined based at least in part on reference images. For example, reference images of stained breast tissue can be used to determine selection criteria used to select nuclei of an image of breast tissue from a subject. In some embodiments, the user can delete any areas of interest on a slide-by-slide basis. For example, a user may visually determine that one or more areas of the image are unsuitable for scoring.

In some embodiments, the facility provides a method for whole slide interpretation of digitized images of tissue data. The method includes receiving a plurality of digitized images of tissue samples. Each tissue sample corresponds to a ground truth slide and for each of the plurality of digitized images, at least one classification associated with the digitized image. The facility is further configured to train a tissue-object classifier using the received digitized images of tissue samples. Upon receiving a digitized image of data associated with a first slide, wherein the first slide is not a ground truth slide, the facility identifies 1) tissue within the digitized image of data associated with the first slide, 2) dominant colors within the identified tissue, and 3) regions within the identified tissue based at least in part on the identified dominant colors. For each of the identified regions, the facility detects seed points within the identified region and extracts objects from the identified regions. Moreover, for each of the extracted objects, the facility can identify characteristics of the extracted object, and using the trained classifier, classify the extracted objects based at least in part on the identified characteristics of the extracted objects.

Moreover, WO 2014102130 application titled "Image analysis for breast cancer prognosis" provides computer-implemented methods for breast cancer prognosis. For example, the method can include generating a breast cancer recurrence prognosis score based at least on measured protein heterogeneity for a biomarker among a plurality of digital fields of view within a displayed image depicting a breast cancer sample detectably labeled with antibodies for the biomarker and an immunohistochemistry combination score for a subject; and outputting an indication of breast cancer recurrence prognosis for the subject based on the breast cancer recurrence prognosis score. Based on these methods, also provided are one or more non-transitory computer-readable media that include computer-executable instructions causing a computing system to perform the disclosed methods.

Also provided are computer-implemented methods. In one example, such methods include a slide image processing tool operable to receive a plurality of slide images depicting protein expression for respective biomarkers in a breast cancer sample from a subject; wherein the slide image processing tool is operable to further receive fields of view within the slide images; wherein the slide image processing tool is operable to calculate an immunohistochemistry combination score based on the slide images and fields of view within the slide images; wherein the slide image processing tool is operable to calculate one or more heterogeneity scores based on the slide images and selections of fields of view within the slide images; and a prognosis tool operable to accept the immunohistochemistry combination score and the one or more heterogeneity scores as input and output an indication of whether cancer is likely to recur in the subject.

The disclosure also provides computer-implemented methods which can include displaying an indication of breast cancer recurrence prognosis. Such methods can include combining an immunohistochemistry combination score and a heterogeneity score into a breast cancer recurrence prognosis score; and displaying an indication of breast cancer recurrence prognosis based on the breast cancer recurrence prognosis score.

Computer-implemented methods are provided that include receiving a plurality of digital fields of view within a displayed image depicting a breast cancer sample detectably labeled with antibodies for a biomarker; measuring protein expression for the biomarker in the digital fields of view; measuring heterogeneity of measured protein expression for the biomarker among the plurality of digital fields of view; and outputting measured protein heterogeneity for the biomarker.

Computer-implemented methods are provided that include calculating an immunohistochemistry combination score for a subject, the method comprising: for a plurality of biomarkers, receiving respective pluralities of digital fields of view within respective images depicting a breast cancer sample detectably labeled with respective biomarker antibodies; measuring percent positivity for a plurality of the biomarkers; calculating the immunohistochemistry combination score, wherein calculating the immunohistochemistry combination score comprises combining the percent positivity for one biomarker with the percent positivity for a second biomarker; and outputting the immunohistochemistry combination score.

Computer-implemented methods are provided that include for ER, receiving a plurality of digital fields of view in an image depicting a breast cancer sample detectably labeled with an antibody for ER; for PR, receiving a plurality of digital fields of view in an image depicting a breast cancer sample detectably labeled with an antibody for ER; for Ki-67, receiving a plurality of digital fields of view in an image depicting a breast cancer sample detectably labeled with an antibody for ER; for HER2, receiving a plurality of digital fields of view in an image depicting a breast cancer sample detectably labeled with an antibody for ER; based on the digital fields of view for ER, calculating an H-score for ER; based on the digital fields of view for PR, calculating a percent positivity for PR; based on the digital fields of view for Ki-67, calculating a percent positivity for Ki-67; based on the digital fields of view for HER2, calculating a binned score for HER2; and combining the H-score for ER, the percent positivity for PR, the percent positivity for Ki-67, and the binned score for HER2 into an immunohistochemistry combination score.

Methods for prognosticating breast cancer in a subject are provided. In some examples, such a method includes selecting in a breast cancer sample obtained from the subject at least two different fields of view (FOVs) for each of estrogen receptor (ER), human epidermal growth factor receptor 2 (HER2), Ki-67 and progesterone receptor (PR), wherein the sample is detectably labeled with antibodies for each of ER, HER2, Ki-67 and PR; measuring ER, HER2, Ki-67 and PR protein expression in each of the selected FOV; determining an immunohistochemistry (IHC) combination score; measuring ER and PR protein heterogeneity in each of the selected FOVs; determining a protein heterogeneity score for each of ER and PR; combining the protein heterogeneity score and the IHC combination score, thereby generating an output prognosis score; and determining that the breast cancer in the subject is likely to be aggressive if the output prognosis score meets a threshold value or determining that the breast cancer in the subject is unlikely to be aggressive if the output prognosis score does not meet the threshold value.

Digital fields of view in images of a breast cancer sample from a subject detectably labeled with antibodies for a biomarker can be received and processed to measure protein heterogeneity for the biomarker. Heterogeneity measurements can be combined with an immunohistochemistry combination score to generate a breast cancer recurrence prognosis score. Such a score can provide more information than the immunohistochemistry combination score standing alone.

Figure 6:
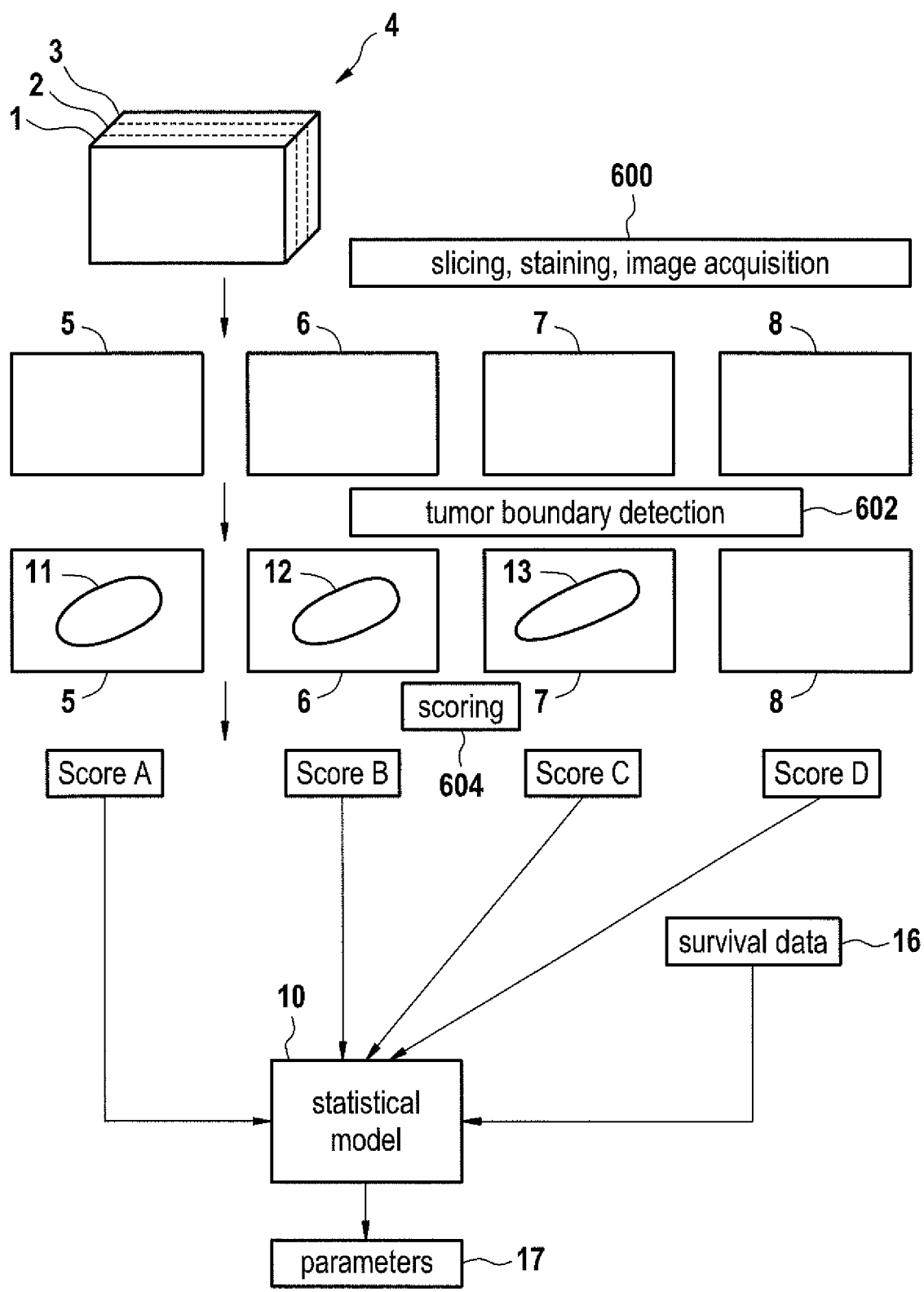
FIG. 6 shows a diagram being illustrative of the generation of a statistical model in accordance with an embodiment of the invention.

FIG. 6 is illustrative of the generation of a statistical model 10, such as a Cox Proportional Hazard Model (cf. FIG. 1). The model is fitted using patient data from a cohort of cancer patients, such as breast cancer patients. The data that is required from each patient comprises survival data and a risk stratification score that is obtained as follows:

A biopsy tissue sample 4 of a patient from the cohort is sliced into neighboring tissue slices to provide tissue slides, such as tissue slides 1, 2, 3 as illustrated in FIG. 6 in step 600. The tissue slices may have a thickness in the micrometer range, such as between 1 μm-10 μm, for example 6 μm.

The tissue slices are stained with a single stain, a stain and a counter-stain or multiple stains. This way e.g. an image that is stained by a stain and a counter-stain and/or a multi-channel image may be obtained.

In the example considered here a single stain image 5 is obtained from tissue slide 1, a single stain image 6 is obtained from tissue slide 2 and a multi-channel image is obtained from tissue slide 3, which—after unmixing—provides at least two unmixed images 7 and 8. These images 5 to 8 may be stored in the electronic memory of an image processing system, such as system 100 (cf. FIG. 1).

It is to be noted that the unmixed images 7 and 8 share exactly the same coordinate system as they are all obtained from the same multi-channel image such that no image registration or image alignment is required within the set of unmixed images. However, image registration is performed with respect to the other images, preferably using one of the unmixed images as a reference.

The images 5, 6 and 7/8 may be registered and aligned using an image registration algorithm in step 600. For example, the multi-channel image 7 is selected as a reference image for performing the image registration algorithm. The image registration algorithm generates a geometrical transformation of each one of the other images, i.e. images 5 and 6 with respect to the multi-channel image. Using the multi-channel image 7 as a reference image for the registration has the advantage that only two alignment operations need be executed in the example considered here. In comparison, when e.g. image 5 would have been selected as the reference image, 3 alignment operations would be required to transform the images 6, 7 and 8 for alignment with image 5. Hence, selecting the multi-channel image as the reference substantially reduces the computational burden and reduces latency times for the image alignments.

In the following step 602 the boundaries of a tumor that is contained in the tissue sample 4 are detected within each one of the images 5 to 8. This provides the tumor boundary 11 for image 5, tumor boundary 12 for image 6 and tumor boundary 13 for the unmixed image 7 which is the same for the unmixed image 8 as images 7 and 8 have been obtained from the same tissue slide 3.

In the following step 604 a score is calculated separately for each one of the images 5 to 8. Only pixels that are located within the respective tumor annotated region boundary are used for the calculation of a respective score. For example, the score A is calculated for the image 5 using only pixels that are located within the tumor boundary 11. Likewise, the score B is calculated for the image 6 using only pixels that are located within the tumor boundary 12 of that image 6. The score C is calculated for image 7 using only pixels that are located within the tumor boundary 13. The score D is calculated for image 8 using the same pixel locations within the boundary 13 as in image 7.

The score of an individual image may be calculated using an analysis algorithms to identify the tumor CELLS within the respective boundary of that image and the subgroup of marker stained tumor CELLS. The slide score of that image is then generated based on these detections.

In the following a risk stratification score is calculated using the individual image scores A, B, C and D. Combining these scores A, B, C and D yields a risk stratification score.

The calculation of the individual scores and their combination into a single score, i.e. the risk stratification score, is obtained by e.g. a statistical Cox model fitting of the individual scores A, B, C, D to the survival outcome data 16 for the patients. The scores A, B, C and D along with survival data 16 of the patient is entered into the statistical model 10. This procedure is carried out for all patients of the cohort of patients.

The statistical model 10 is then fitted using these data entries which provides a set of model parameters 17 that may be stored on a database (cf. database 116 of FIG. 1).

The weights, i.e. the parameter values, on how to combine the scores and calculate a single risk stratification score, are obtained by doing a statistical Cox model fitting of the tissue scores to the survival outcome data for the training cohort. So, the weights we come up with are quite different from the ones that are published in the prior art as the weights are dependent on the workflow used.

In particular, the weights will be different from the whole tumor analysis to the weights that will be used with the Ki67 hot spot analysis.

In accordance with an embodiment of the invention image 5 is obtained from an H&E slide. The tumor boundary detection is performed using the H&E stained slide by applying an image processing algorithm onto the image 5 that detects the tumor boundary 11 or by manual entry. Next, the tumor boundaries 12 and 13 are identified in the images 6 and 7, respectively, using the tumor boundary 11. For example, images 6 and 7 are obtained from tissue slides that have different stains and in which the detection of the tumor boundary is more difficult than in the H&E image 5.

Using the tumor boundary 11 of image 5 as an input value for the detection of the respective tumor boundaries 12 and 13, such as by inter-marker registration, facilitates the detection of the tumor boundaries in the images 6 and 7 which provides a more precise result.

This may be accomplished in accordance with A. Sarkar, Q. Yuan and C. Srinivas, "A robust method for inter-marker whole slide registration of digital pathology images using lines based features," 2014 IEEE 11th International Symposium on Biomedical Imaging (ISBI), Beijing, 2014, pp. 762-765, doi: 10.1109/ISBI.2014.6867982.

The fitting of the statistical model 10 using the entered data, including the survival data 16, is as such known from the prior art, c.f. Breslow, N. E. "Analysis of Survival Data under the Proportional Hazards Model." International Statistical Review/Revue Internationale De Statistique, vol. 43, no. 1, 1975, pp. 45-57. JSTOR.

As a result of the execution of the method illustrated in FIG. 6 a fitted statistical model 10 is obtained.

Figure 7:
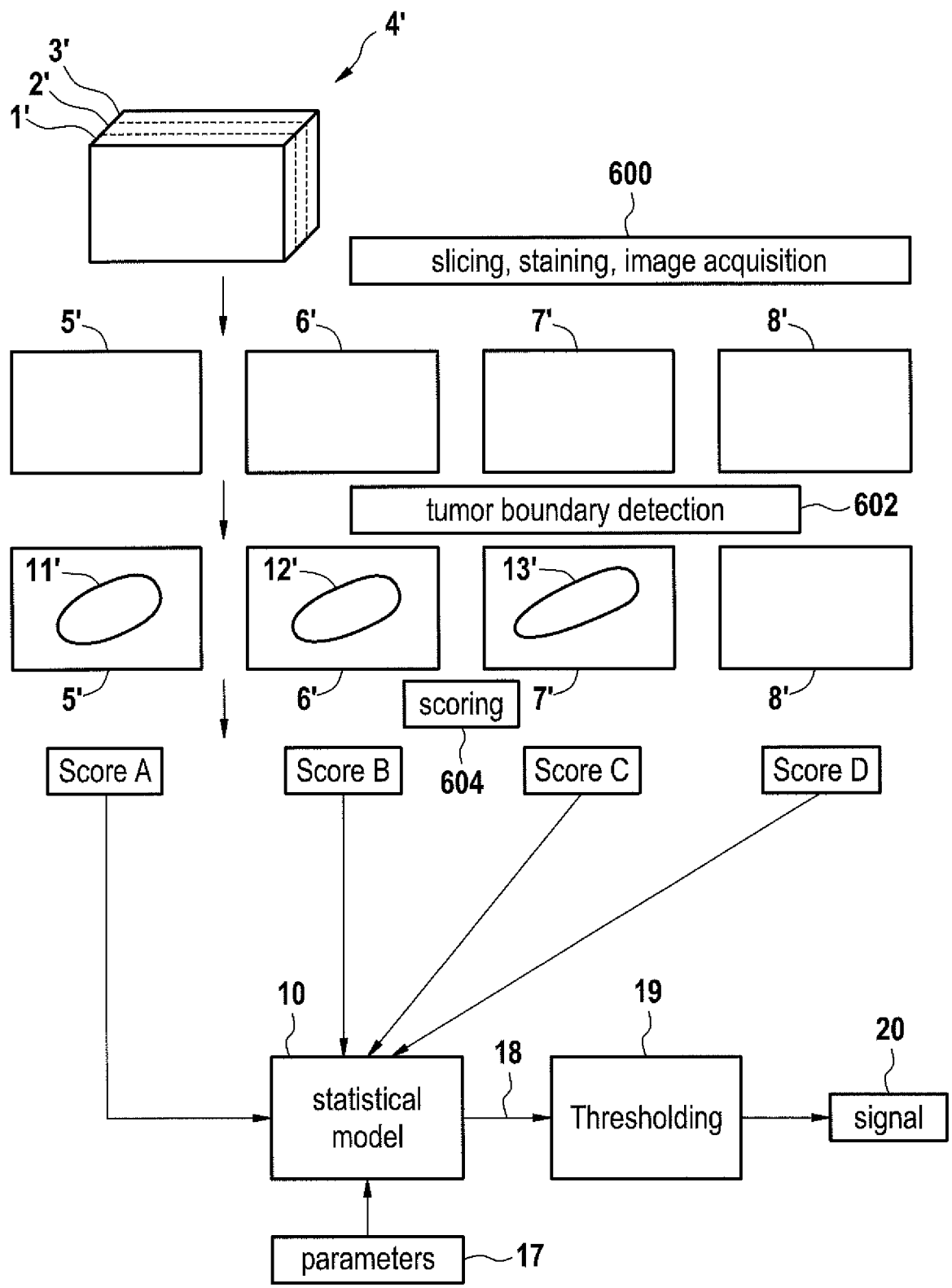
FIG. 7 is a diagram being illustrative of an digital pathology enabled method for analyzing a cancer biopsy tissue sample obtained from a patient in accordance with embodiments of the invention.

FIG. 7 is illustrative of an image processing method in which the fitted statistical model 10 is utilized. Analogous to the method of FIG. 6, a biopsy tissue sample 4' is processed for a patient. The biopsy tissue sample 4' is sliced to provide tissue slides 1', 2' and 3' in the same way as it was done for the cohort of patients that served to generate the statistical model 10.

Likewise, the following steps 600, 602, 604 are also performed in the same way on the respective images 5', 6', 7' and 8' that result from the tissue slides 1', 2' and 3' of that patient from which the biopsy tissue sample 4' has been obtained.

The resultant scores A, B, C and D are entered into the fitted statistical model 10. The parameters 17 are read from memory, such as from database 116 (cf. FIG. 1) and the statistical model 10 is executed automatically, such as by the system 100 (cf. FIG. 1) using the parameters 17 and the entered scores A, B, C and D.

As a result, the statistical model 10 provides an output value 18, i.e. the risk stratification score, that may be a percentage value or a value between 0 and 1.

The output value 18 is then thresholded by the system 100 by execution of a program module 19. The threshold value used for performing the thresholding operation by the module 19 is a cut-off point that has been determined on the basis of the clinical data that has been collected for the generation of the statistical model 10.

The resultant output signal 20 that is output by the thresholding module 19 is binary whereby for example logical '0' indicates that the patient from which the biopsy tissue sample 4' has been obtained belongs to a low-risk group of patients such that reoccurrence of the cancer of that patient is not to be expected whereas the logical value of '1' of the signal 20 may indicate that the patient belongs to a high-risk group such that the administration of a drug, such as adjuvant chemotherapy, is recommended.

In accordance with a further embodiment of the invention the images 5 and 5' are obtained from Ki-67 stained tissue slides. Instead of the tumor and tumor boundary, a Ki-67 hot spot and Ki-67 hot spot boundaries are detected in the images analogously to the above described procedures.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

The invention claimed is:

1. A digital pathology method for analyzing a cancer biopsy tissue sample of a subject, the method comprising:
    acquiring multiple images from histopathological tissue slides of the biopsy tissue sample, wherein each image of the multiple images corresponds to a histopathological tissue slide representing a tissue slice of the biopsy tissue sample;
    selecting a field of view in one of the images for analysis, wherein the field of view comprises a tumor or a hot spot and the image represents at least a portion of a histopathological tissue slide that is stained with a first type of stain for a first biomarker;
    detecting a boundary of the tumor or the hot spot in the image;
    applying the detected boundary of the image to other images of the multiple images to identify boundaries of the tumor or the hot spot in each image of the other images, at least one of the other images of the multiple images representing at least a portion of another histopathological tissue slide that is stained with a second type of stain for a second biomarker, wherein the first type of stain, the second type of stain, the field of view, or any combination thereof defines a workflow for analyzing the cancer biopsy tissue;
    determining multiple slide scores for each of the multiple images based on the workflow, wherein the determining the slide scores for each of the multiple images comprises detecting and classifying, using a machine-learning model, cells as positive or negative for the first biomarker and/or the second biomarker using only a set of pixels that represent an image portion within the boundary of the tumor or hot spot;
    obtaining a statistical model based on the workflow, wherein the statistical model is configured to model a cancer reoccurrence risk based on the first type of stain, the second type of stain, the field of view, or any combination thereof;
    retrieving, from memory, a subset of parameter values for the statistical model based on the workflow, wherein the subset of parameter values are associated with the first type of stain, the second type of stain, the field of view, or any combination thereof, and the subset of parameter values are only a portion of all parameter values retrievable from the memory;
    entering the subset of parameter values and the slide scores into the statistical model;
    executing the statistical model using the subset of parameter values and the slide scores, wherein the executing the statistical model comprises modeling an impact of the slide scores on survival probability time to distant recurrence, and calculating a risk stratification score based on the modeling; and
    generating a signal by thresholding the risk stratification score, wherein the signal indicates either that the subject from which the cancer biopsy tissue sample has been obtained belongs to a low-risk group of patients such that reoccurrence of cancer within the subject is not to be expected or the subject belongs to a high-risk group.

2. The method of claim 1, wherein the first type of stain includes a hematoxylin and eosin (H&E) stain and the second type of stain includes an immunohistochemical (IHC) stain.

3. The method of claim 1, wherein the multiple slide scores comprise marker percent positivity, H-scores, and regional heterogeneity determined based on the cells being positive or negative for the first biomarker and/or the second biomarker.

4. The method of claim 3, further comprising combining the multiple slide scores generate a combined score for the histopathological tissue slides, and the combined score is entered into the statistical model.

5. The method of claim 1, wherein the subset of parameter values were fitted by training the statistical model on a training cohort of images, and wherein the training comprised comparing slide scores for the training cohort of images with survival data of each of a plurality of patients comprising populations of high and low risks to determine whole-slide scoring algorithms for the statistical model depending on a field of view identified comprising either a tumor or a hot spot.

6. A system for analyzing a cancer biopsy tissue sample of a subject, the system comprising:
    one or more data processors; and
    a non-transitory computer readable storage medium containing instructions which, when executed on the one or more data processors, cause the one or more data processors to perform the following operations:

acquiring multiple images from histopathological tissue slides of the biopsy tissue sample, wherein each image of the multiple images corresponds to a histopathological tissue slide representing a tissue slice of the biopsy tissue sample;

selecting a field of view in one of the images for analysis, wherein the field of view comprises a tumor or a hot spot and the image represents at least a portion of a histopathological tissue slide that is stained with a first type of stain for a first biomarker;

detecting a boundary of the tumor or the hot spot in the image;

applying the detected boundary of the image to other images of the multiple images to identify boundaries of the tumor or the hot spot in each image of the other images, at least one of the other images of the multiple images representing at least a portion of another histopathological tissue slide that is stained with a second type of stain for a second biomarker, wherein the first type of stain, the second type of stain, the field of view, or any combination thereof defines a workflow for analyzing the cancer biopsy tissue;

determining multiple slide scores for each of the multiple images based on the workflow, wherein the determining the slide scores for each of the multiple images comprises detecting and classifying, using a machine-learning model, cells as positive or negative for the first biomarker and/or the second biomarker using only a set of pixels that represent an image portion within the boundary of the tumor or hot spot;

obtaining a statistical model based on the workflow, wherein the statistical model is configured to model a cancer reoccurrence risk based on the first type of stain, the second type of stain, the field of view, or any combination thereof;

retrieving, from memory, a subset of parameter values for the statistical model based on the workflow, wherein the subset of parameter values are associated with the first type of stain, the second type of stain, the field of view, or any combination thereof, and the subset of parameter values are only a portion of all parameter values retrievable from the memory;

entering the subset of parameter values and the slide scores into the statistical model;

executing the statistical model using the subset of parameter values and the slide scores, wherein the executing the statistical model comprises modeling an impact of the slide scores on survival probability time to distant recurrence, and calculating a risk stratification score based on the modeling; and generating a signal by thresholding the risk stratification score, wherein the signal indicates either that the subject from which the cancer biopsy tissue sample has been obtained belongs to a low-risk group of patients such that reoccurrence of cancer within the subject is not to be expected or the subject belongs to a high-risk group.

7. The system of claim 6, wherein the first type of stain includes a hematoxylin and eosin (H&E) stain and the second type of stain includes an immunohistochemical (IHC) stain.

8. The system of claim 6, wherein the multiple slide scores comprise marker percent positivity, H-scores, and regional heterogeneity determined based on the cells being positive or negative for the first biomarker and/or the second biomarker.

9. The system of claim 8, wherein the operations further comprise combining the multiple slide scores generate a combined score for the histopathological tissue slides, and the combined score is entered into the statistical model.

10. The system of claim 6, wherein the subset of parameter values were fitted by training the statistical model on a training cohort of images, and wherein the training comprised comparing slide scores for the training cohort of images with survival data of each of a plurality of patients comprising populations of high and low risks to determine whole-slide scoring algorithms for the statistical model depending on a field of view identified comprising either a tumor or a hot spot.

11. A computer-program product for analyzing a cancer biopsy tissue sample of a subject, the computer-program product tangibly embodied in a non-transitory machine-readable storage medium, including instructions configured to cause one or more data processors to perform the following operations:

acquiring multiple images from histopathological tissue slides of the biopsy tissue sample, wherein each image of the multiple images corresponds to a histopathological tissue slide representing a tissue slice of the biopsy tissue sample;

selecting a field of view in one of the images for analysis, wherein the field of view comprises a tumor or a hot spot and the image represents at least a portion of a histopathological tissue slide that is stained with a first type of stain for a first biomarker;

detecting a boundary of the tumor or the hot spot in the image;

applying the detected boundary of the image to other images of the multiple images to identify boundaries of the tumor or the hot spot in each image of the other images, at least one of the other images of the multiple images representing at least a portion of another histopathological tissue slide that is stained with a second type of stain for a second biomarker, wherein the first type of stain, the second type of stain, the field of view, or any combination thereof defines a workflow for analyzing the cancer biopsy tissue;

determining multiple slide scores for each of the multiple images based on the workflow, wherein the determining the slide scores for each of the multiple images comprises detecting and classifying, using a machine-learning model, cells as positive or negative for the first biomarker and/or the second biomarker using only a set of pixels that represent an image portion within the boundary of the tumor or hot spot;

obtaining a statistical model based on the workflow, wherein the statistical model is configured to model a cancer reoccurrence risk based on the first type of stain, the second type of stain, the field of view, or any combination thereof;

retrieving, from memory, a subset of parameter values for the statistical model based on the workflow, wherein the subset of parameter values are associated with the first type of stain, the second type of stain, the field of view, or any combination thereof, and the subset of parameter values are only a portion of all parameter values retrievable from the memory;

entering the subset of parameter values and the slide scores into the statistical model;

executing the statistical model using the subset of parameter values and the slide scores, wherein the executing the statistical model comprises modeling an impact of the slide scores on survival probability time to distant recurrence, and calculating a risk stratification score based on the modeling; and generating a signal by thresholding the risk stratification score, wherein the signal indicates either that the subject from which the cancer biopsy tissue sample has been obtained belongs to a low-risk group of patients such that reoccurrence of cancer within the subject is not to be expected or the subject belongs to a high-risk group.

12. The system of claim 11, wherein the first type of stain includes a hematoxylin and eosin (H&E) stain and the second type of stain includes an immunohistochemical (IHC) stain.

13. The system of claim 11, wherein the multiple slide scores comprise marker percent positivity, H-scores, and regional heterogeneity determined based on the cells being positive or negative for the first biomarker and/or the second biomarker.

14. The system of claim 13, wherein the operations further comprise combining the multiple slide scores generate a combined score for the histopathological tissue slides, and the combined score is entered into the statistical model.

15. The system of claim 11, wherein the subset of parameter values were fitted by training the statistical model on a training cohort of images, and wherein the training comprised comparing slide scores for the training cohort of images with survival data of each of a plurality of patients comprising populations of high and low risks to determine whole-slide scoring algorithms for the statistical model depending on a field of view identified comprising either a tumor or a hot spot.

* * * * *